US009808570B2

(12) United States Patent
Head et al.

(10) Patent No.: US 9,808,570 B2
(45) Date of Patent: Nov. 7, 2017

(54) SYRINGE STORAGE TRAY

(71) Applicants: BAXALTA GMBH, Opfikon (CH); BAXALTA INCORPORATED, Bannockburn, IL (US)

(72) Inventors: Brian R Head, Salem, WI (US); Mark E Williamson, Wonder Lake, IL (US); Michael P Wehrli, Cary, IL (US); Joseph J. Kircher, Gurnee, IL (US); Michelle L. Moran, Libertyville, IL (US); Atif M. Yardimci, Lake Forest, IL (US)

(73) Assignees: Baxalta Incorporated, Bannockburn, IL (US); Baxalta GmbH, Opfikon (CH)

( * ) Notice: Subject to any disclaimer, the term of this patent is extended or adjusted under 35 U.S.C. 154(b) by 291 days.

(21) Appl. No.: 14/086,947

(22) Filed: Nov. 21, 2013

(65) Prior Publication Data
US 2014/0078854 A1 Mar. 20, 2014

Related U.S. Application Data

(63) Continuation-in-part of application No. PCT/US2012/070804, filed on Dec. 20, 2012.
(Continued)

(51) Int. Cl.
*A61M 5/00* (2006.01)
*B01F 11/00* (2006.01)
(Continued)

(52) U.S. Cl.
CPC ........ *A61M 5/002* (2013.01); *A61M 5/31501* (2013.01); *B01F 11/0005* (2013.01); *A61M 5/008* (2013.01); *A61M 2005/3104* (2013.01)

(58) Field of Classification Search
CPC .................................................... A61M 5/002
See application file for complete search history.

(56) References Cited

U.S. PATENT DOCUMENTS 2,856,925 A 10/1958 Helmer
3,372,798 A 3/1968 Thomas
(Continued)

FOREIGN PATENT DOCUMENTS

EP 1595561 11/2005
EP 1930040 6/2008
(Continued)

OTHER PUBLICATIONS

International Preliminary Report on Patentability, International Application No. PCT/US2012/070804, dated Nov. 25, 2014.
(Continued)

*Primary Examiner* — Abbas Rashid
(74) *Attorney, Agent, or Firm* — Troutman Sanders LLP

(57) ABSTRACT

A storage system is provided. The system may include a tray having at least one recess in which at least one syringe is disposed, the syringe including a barrel with first and second barrel ends, and a stopper fixedly disposed between the first and second barrel ends. A tool attached to the stopper through the second barrel end, the tool having a first end attached to the stopper and a second end attached to or abutting the barrel or a surface of the recess, the first end being selectively adjustable relative to the second end to vary the distance between the first and second ends of the tool. In addition or in the alternative to the tool, the system may include a motion generator attached externally to the syringe, the motion generator being one of at least a vibration generator and a rotating frame.

1 Claim, 17 Drawing Sheets

Related U.S. Application Data

(60) Provisional application No. 61/649,586, filed on May 21, 2012.

(51) Int. Cl.
*A61M 5/315* (2006.01)
*A61M 5/31* (2006.01)

(56) References Cited

U.S. PATENT DOCUMENTS

| | | | |
|---|---|---|---|
| 3,770,026 A | 11/1973 | Isenberg | |
| 3,820,652 A | 6/1974 | Thackston | |
| 4,073,321 A | 2/1978 | Moskowitz | |
| 4,246,898 A | 1/1981 | Travalent | |
| 4,563,178 A | 1/1986 | Santeramo | |
| 4,589,870 A * | 5/1986 | Citrin | B05C 17/0126 222/309 |
| 4,657,138 A | 4/1987 | Watson | |
| 4,671,408 A | 6/1987 | Raines et al. | |
| 4,753,345 A | 6/1988 | Goodsir et al. | |
| 4,767,008 A | 8/1988 | Warnecke et al. | |
| 4,863,451 A | 9/1989 | Marder | |
| 4,921,487 A * | 5/1990 | Buffet | A61M 5/1452 128/DIG. 12 |
| 5,007,535 A | 4/1991 | Meseke et al. | |
| 5,133,454 A | 7/1992 | Hammer | |
| 5,156,267 A | 10/1992 | Yates, Jr. et al. | |
| 5,293,993 A | 3/1994 | Yates, Jr. et al. | |
| 5,356,383 A * | 10/1994 | Daly | A61M 5/24 206/366 |
| 5,385,558 A | 1/1995 | Cottone, Sr. | |
| 5,385,559 A * | 1/1995 | Mannix | A61M 5/1782 141/27 |
| 5,772,031 A | 6/1998 | Landis | |
| 5,882,338 A * | 3/1999 | Gray | A61M 5/1456 604/131 |
| 6,228,324 B1 * | 5/2001 | Hasegawa | A61L 2/208 206/364 |
| 6,500,153 B1 * | 12/2002 | Sheppard | A61B 17/3401 604/164.01 |
| 6,581,648 B1 * | 6/2003 | Zolentroff | A61J 1/2096 141/2 |
| 6,585,696 B2 | 7/2003 | Petersen et al. | |
| 6,595,362 B2 | 7/2003 | Penney et al. | |
| 7,018,089 B2 | 3/2006 | Wenz | |
| 7,048,120 B2 | 5/2006 | Pond | |
| 7,476,218 B2 | 1/2009 | Bloom | |
| 7,597,196 B2 | 10/2009 | Langone | |
| 8,216,192 B2 * | 7/2012 | Burroughs | A61M 5/1782 604/201 |
| 8,672,881 B2 | 3/2014 | Nagamatsu | |
| 8,974,424 B2 | 3/2015 | Soma | |
| 2001/0051789 A1 * | 12/2001 | Parsons | A61M 5/30 604/68 |
| 2002/0108875 A1 | 8/2002 | Feinberg et al. | |
| 2002/0185406 A1 * | 12/2002 | Massengale | A61B 19/026 206/571 |
| 2004/0004019 A1 * | 1/2004 | Busch | A61B 17/3401 206/571 |
| 2004/0238391 A1 * | 12/2004 | Pond | A61C 3/005 206/369 |
| 2007/0185495 A1 * | 8/2007 | Hess | A61M 5/008 606/93 |
| 2008/0125722 A1 | 5/2008 | Hess et al. | |
| 2009/0093757 A1 * | 4/2009 | Tennican | A61J 1/2096 604/87 |
| 2009/0227958 A1 * | 9/2009 | Burroughs | A61M 5/1782 604/201 |
| 2009/0326479 A1 * | 12/2009 | Janish | A61M 5/31511 604/218 |
| 2010/0012537 A1 | 1/2010 | Farrar et al. | |
| 2010/0181218 A1 | 7/2010 | Beccaro et al. | |
| 2010/0191182 A1 * | 7/2010 | Smith | A61J 1/2096 604/87 |
| 2013/0245492 A1 * | 9/2013 | Klenk | A61M 5/31586 600/556 |
| 2014/0166514 A1 | 6/2014 | Martin et al. | |
| 2014/0224688 A1 | 8/2014 | Slemmen et al. | |
| 2014/0352724 A1 * | 12/2014 | Meyer | A61B 19/34 134/8 |
| 2015/0129442 A1 * | 5/2015 | Head | A61M 5/002 206/366 |

FOREIGN PATENT DOCUMENTS

| | | |
|---|---|---|
| JP | 8207960 | 8/1996 |
| JP | 2001104475 | 4/2001 |
| JP | 2007290720 | 11/2007 |
| JP | 2008067989 | 3/2008 |
| JP | 2011006154 | 1/2011 |
| WO | WO 2007/130809 | 11/2007 |

OTHER PUBLICATIONS

International Search Report and Written Opinion, international application No. PCT/US2012/070804, mailing date Jun. 4, 2013.

* cited by examiner

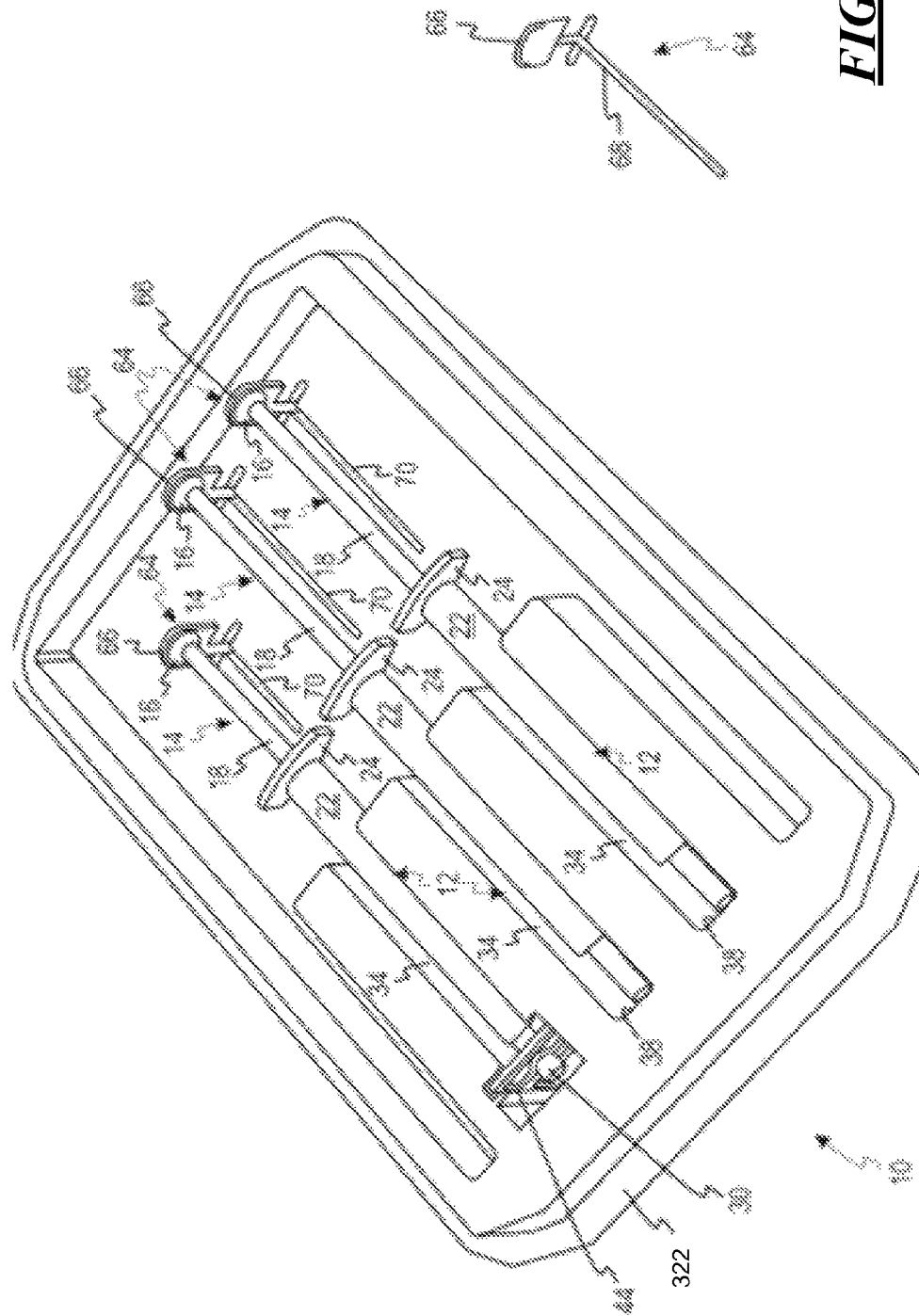

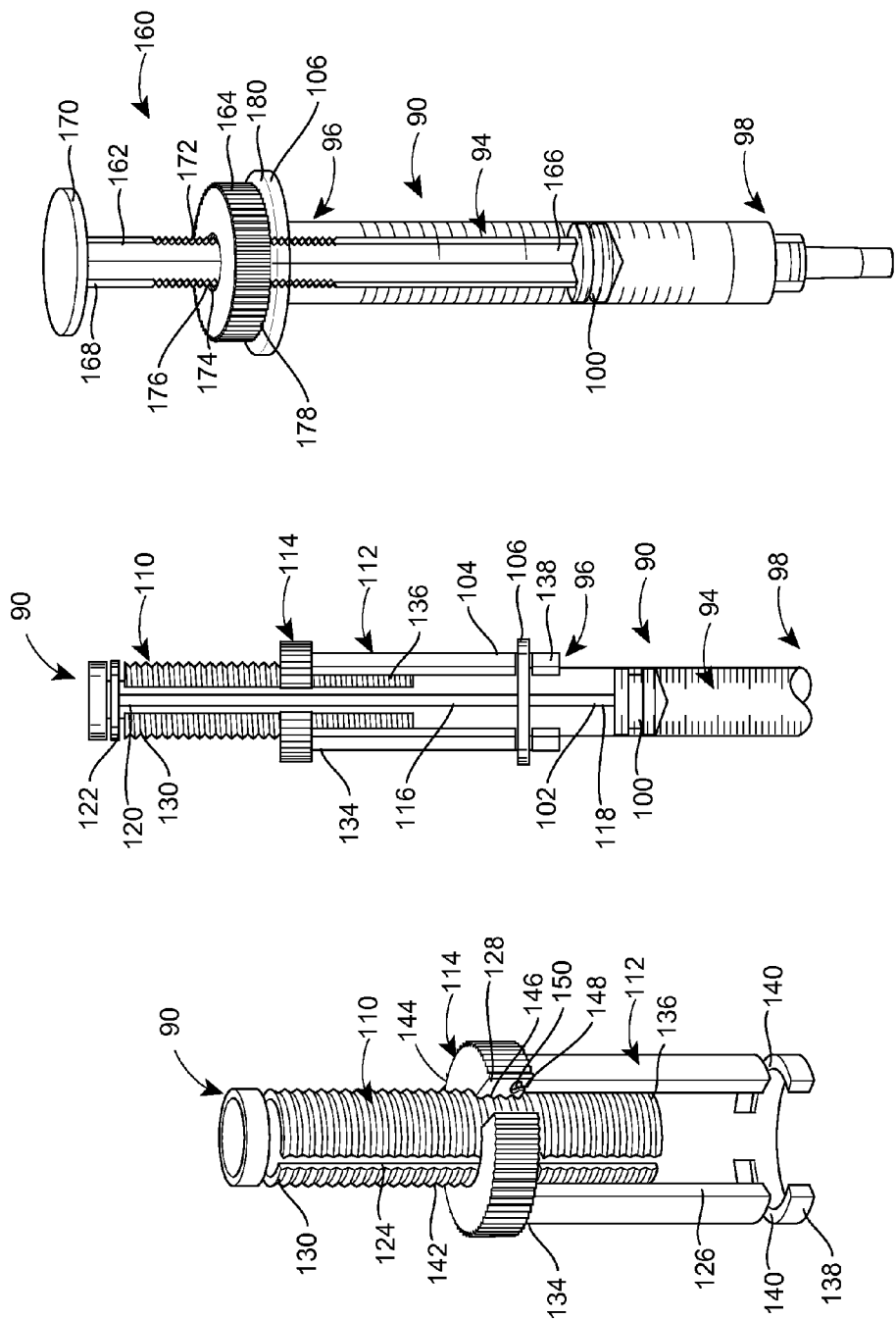

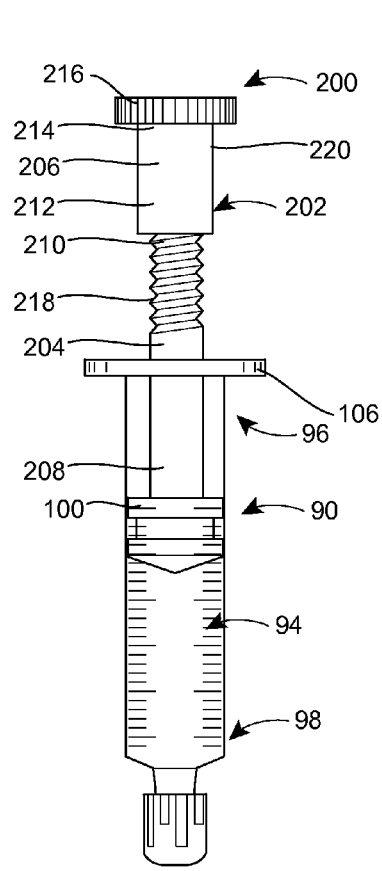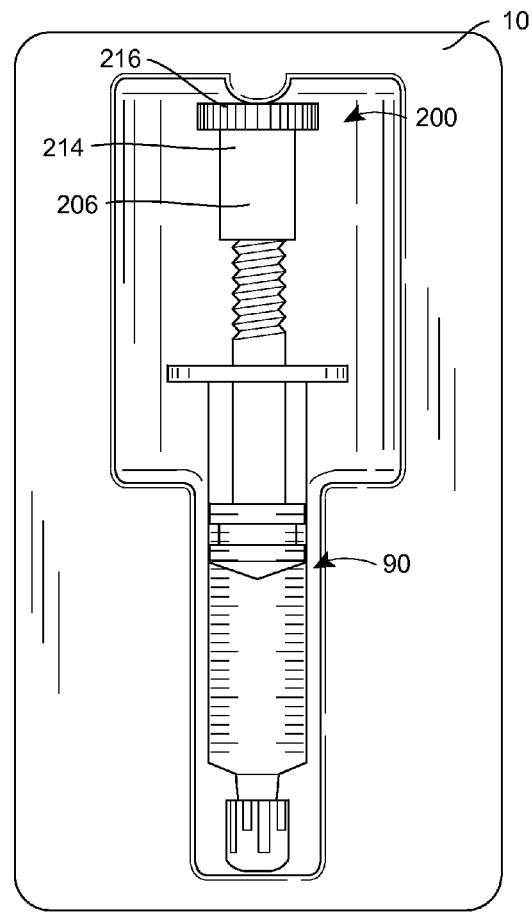
*FIG. 10*  *FIG. 10a*

SYRINGE STORAGE TRAY

FIELD OF THE DISCLOSURE

This disclosure relates to a storage and handling system for one or more syringes and, more particularly, a storage tray for one or more prefilled syringes.

BACKGROUND

Prefilled syringes are increasingly being used as an alternative to vial-based systems. Prefilled syringes have the potential to both minimize the potential of microbial contamination and reduce medication dosing errors, while also providing enhanced convenience and ease of use. Further, the use of prefilled syringes is likely to reduce the amount of overfill when compared to single-dose vials, leading to the optimization of the number of doses that may be obtained from a given volume of the substance to be administered. These advantages of prefilled syringes are especially valuable when the substances to be administered are of a high cost and/or prepared in small quantities, such as gene-based and cellular biologic medical products which may be created from the patient's own stem cells.

Once prefilled, a safe and effective system for handling and delivery of the prefilled syringes to the patient is required. In particular, the relative position of the plunger to the barrel of the syringe must be substantially fixed during shipment to help insure the sterility of the syringe and its contents. When the substances contained in the syringes are high value product, such as biologics, this becomes even more important. Pursuant to the present disclosure a handling and delivery system is provided that includes an improved tray for storage and shipment of one or more prefilled syringes.

SUMMARY OF THE DISCLOSURE

In accordance with an aspect of the disclosure, a storage system for at least one syringe is provided, the syringe including a barrel with first and second barrel ends, and a stopper disposed between the first and second barrel ends. The system may include a tray having at least one recess in which the at least one syringe is disposed. The system may also include a tool attached to the stopper through the second barrel end to limit the movement of the stopper toward either one or both of the first and second barrel ends. The tool may have a first end attached to the stopper and a second end attached to or abutting the barrel or a surface of the at least one recess, the first end being selectively adjustable relative to the second end to vary the distance between the first and second ends of the tool.

In accordance with another aspect, the tool may include a shaft having first and second shaft sections, a first end of the first shaft section attached to the stopper, a second end of the first shaft section threadingly engaging a first end of the second shaft section, and a second end of the second shaft section abutting a surface of the at least one recess.

In accordance with another aspect, the syringe may have a rim disposed at the second barrel end, and the tool may include a shaft having a first shaft end attached to the stopper and a second shaft end, and a wheel abutting the rim of the syringe and having a passage through which the shaft is disposed, the passage threadingly engaging the shaft.

In accordance with another aspect, the tool may include a shaft having a first shaft end attached to the stopper and a second shaft end, an inner collar with the shaft disposed within the inner collar and the inner collar having a first inner collar end abutting the second shaft end, and an outer collar with the inner collar disposed within the outer collar and the outer collar having a first outer collar end threadingly engaging a second inner collar end and a second outer collar end attached to the barrel.

In a further aspect, a storage system may include a tray having at least one recess in which at least one syringe is disposed, the syringe including a barrel with first and second barrel ends, and a stopper fixedly disposed between the first and second barrel ends. The system may further include a motion generator attached externally to the at least one syringe, the motion generator being one of at least a vibration generator and a rotating frame.

In accordance with another aspect, the vibration generator may include a plurality of transducers disposed along the barrel between the first and second barrel ends and a controller coupled to the transducers to selectively activate the transducers.

In accordance with another aspect, the rotating frame may include a circular table having first and second opposing faces bounded by a circular rim, and an arm attached at a first end to the first face and at a second end to a pivot, the tray attached to the second face of the circular table.

In accordance with another aspect, the rotating frame may include a shaft disposed within the housing having an outer shaft surface and a drive attached to the shaft, the tray has a cylindrical shape and is disposed between an inner housing surface of a tubular housing and the outer shaft surface with tray abutting the inner housing surface and the outer shaft surface.

BRIEF DESCRIPTION OF THE DRAWINGS

These and other aspects of the present subject matter are described in the following detailed description and shown in the attached figures, of which:

FIGS. 5-7 are perspective views similar to FIG. 1 showing features that may be used in combination with or as an alternative to the various features incorporated into the syringe tray of FIGS. 1-4.

FIG. 7a is a perspective view of a clip that may be used in combination with the embodiment shown in FIG. 7.

FIGS. 8 and 8a are perspective views of a tool that may be used in combination with any of the syringe trays of FIGS. 5-7.

FIG. 9 is a perspective view of the tool that may be used in combination with any of the syringe trays of FIGS. 5-7.

FIGS. 10 and 10a are perspective views of a tool that may be used in combination with any of the syringe trays of FIGS. 5-7.

DETAILED DESCRIPTION

A more detailed description of a syringe storage tray in accordance with the present disclosure is set forth below. It should be understood that the description below of various specific embodiments is intended to be exemplary, and not exhaustive of all possible variations. Thus, the scope of the disclosure is not intended to be limiting, and should be understood to encompass further variations or embodiments that would occur to persons of ordinary skill.

Turning to the drawings, there is seen a syringe storage tray, generally designated 10, in accordance with the present disclosure. The tray 10 may be thermoformed from a plastic material, such as, for example, PETE (polyethylene therephthalate) or PETG (polyethylene therephthalate glycol), or any other material which provides the tray with the desired structural integrity, is readily susceptible to sterilization, and is easily disposed of or recycled.

Figure 1:
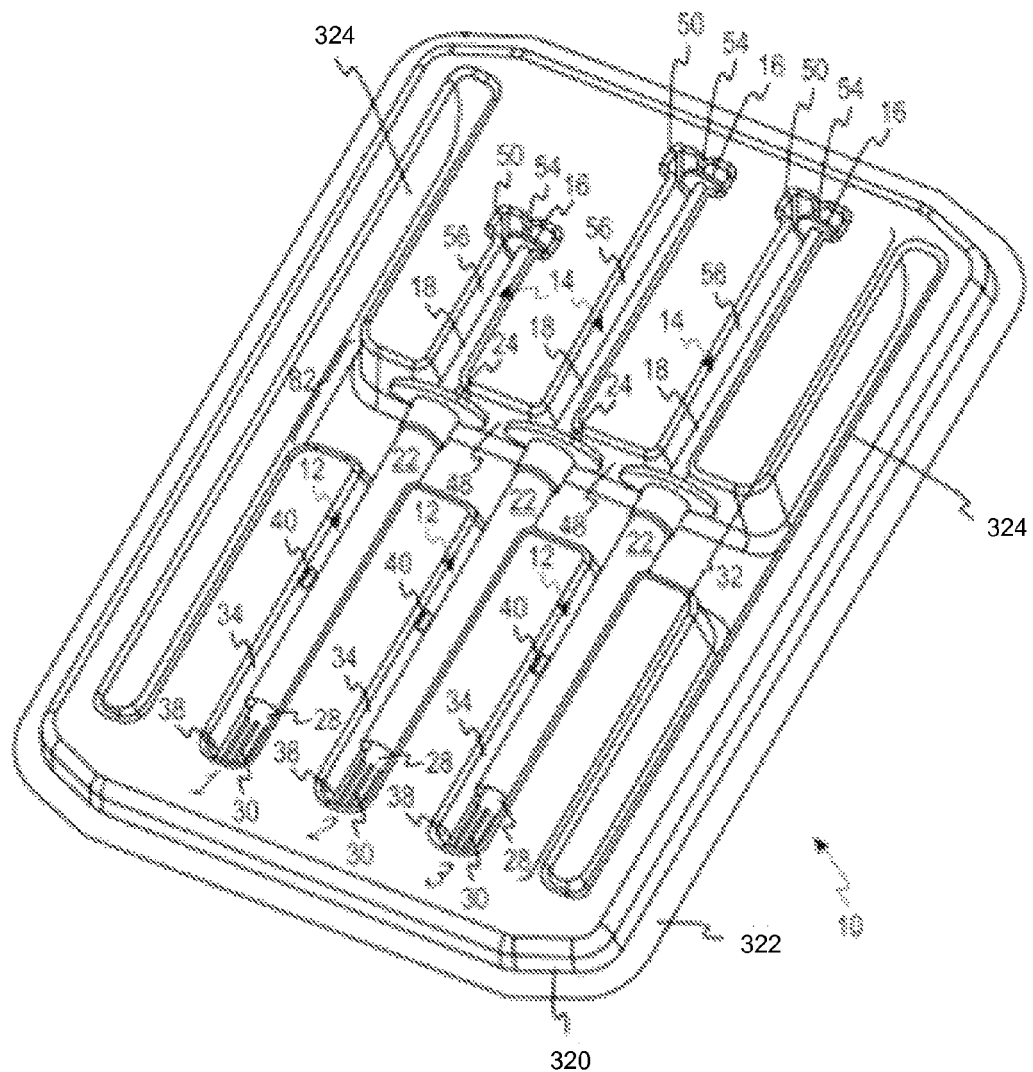
FIG. 1 is a perspective view of a syringe storage tray according to the present disclosure in combination with three prefilled syringes.
Figure 2:
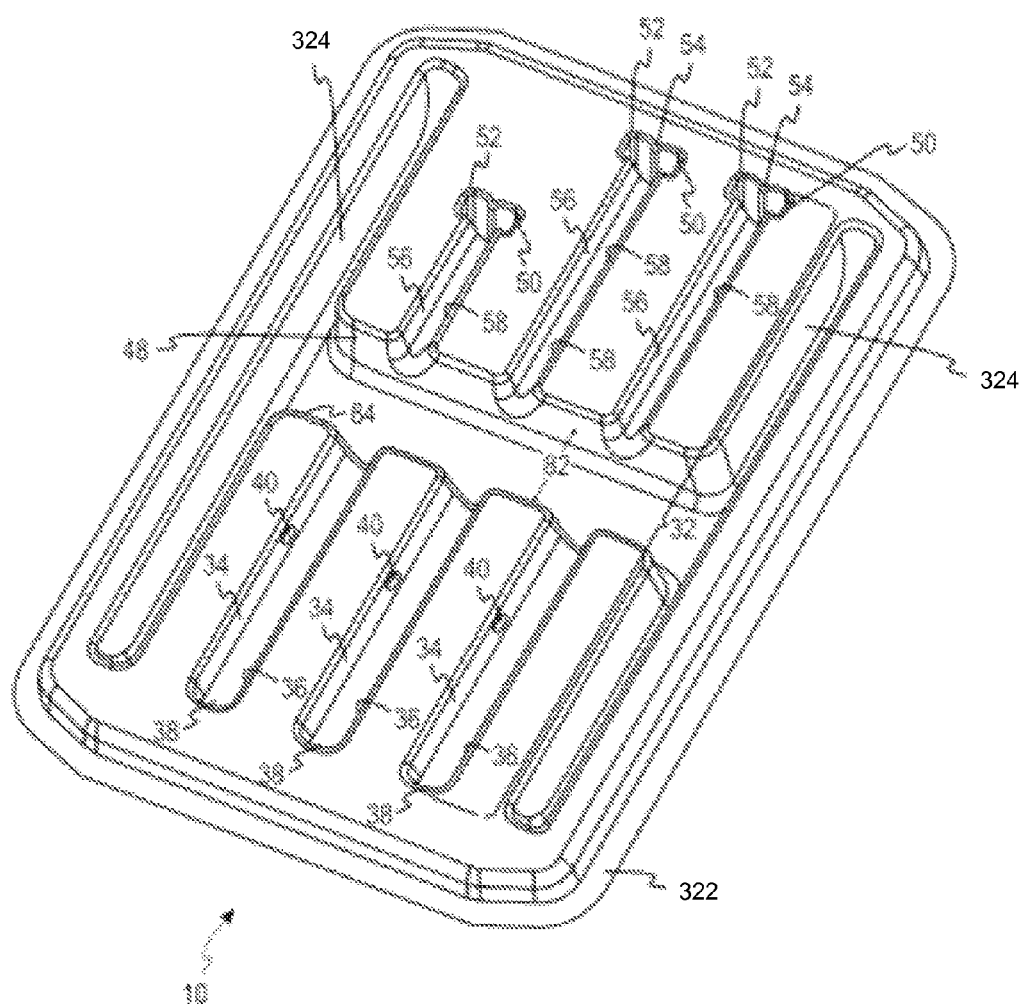
FIG. 2 is a perspective view of a syringe storage tray similar to FIG. 1, except that the prefilled syringes have been removed.
Figure 3:
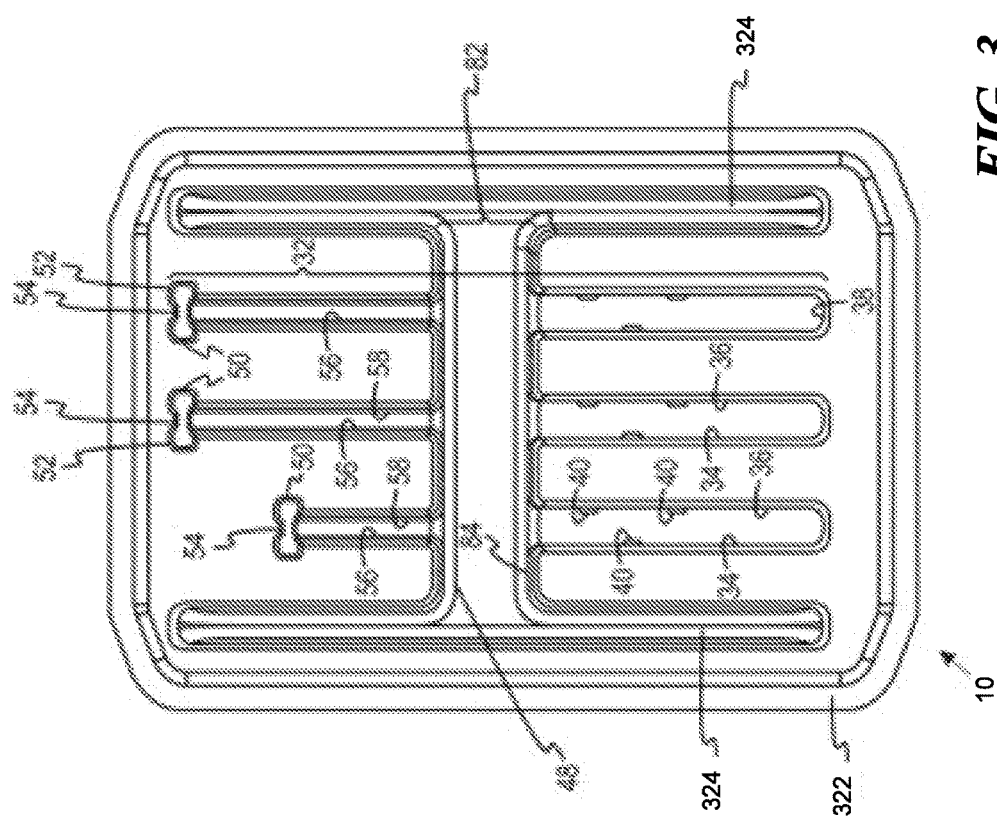
FIG. 3 is a plan view of the syringe storage tray of FIG. 2.
Figure 4:
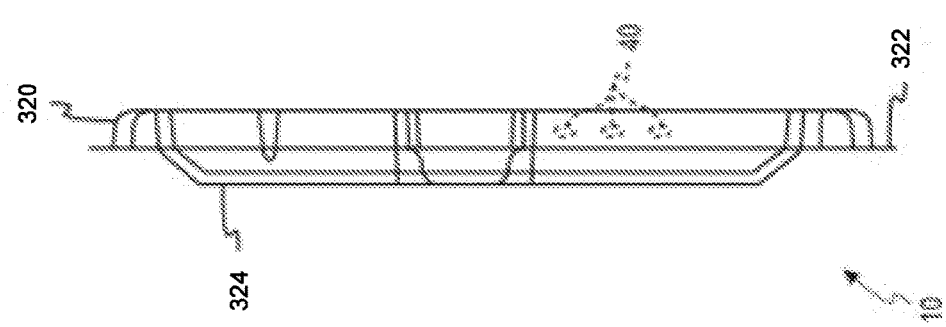
FIG. 4 is a side view of the syringe storage tray of FIG. 2.

As shown in FIG. 1, the storage tray 10 is configured to receive one or more prefilled syringes 12 (with three being shown). As is typical, each illustrated syringe 12 comprises a plunger 14 having a thumb rest 16 on one end of a shaft 18 and a piston or stopper (not seen) on the other end. The piston is received within the bore of a barrel 22, the barrel 22 being formed with opposed finger flanges 24 on one end and a luer lock 28 on the other end. A sheath or cap 30 is received in luer lock 28 and is removed prior to use.

In accordance with the disclosure, and with reference generally to FIGS. 1-4, the tray 10 comprises a recess, generally designated 32, for receipt of each syringe that is to be carried by the tray 10. It is contemplated that a syringe tray as described herein may be used to hold syringes prefilled with a patient's stem cells, the syringes being configured to be connected to a percutaneous transluminal catheter for the transport of the stem cells to the patient's ischemic tissue, for example, cardiac tissue. As illustrated, the tray has three recesses 32, but it could have either more or less depending on, e.g., whether the agent to be administered has multiple components or if multiple doses are to be administered. Thus, a syringe storage tray according to the present disclosure could be configured with one or more recesses 32. Each of the three recesses 12 for the illustrated tray 10 has generally the same configuration. Thus, identical reference numerals will be used to designate structure common to each recess 12.

Each recess 32 preferably comprises three segments: a first segment for holding the syringe barrel 22, a second segment for holding the plunger 14 in a pre-determined axial relation to the barrel, and a third segment intermediate the first and second segments configured to provide access to the portion of the barrel 22 adjacent the finger flanges 24 sufficient to permit the barrel to be gripped by the fingers of a user to remove the syringe from the tray.

Figure 5:
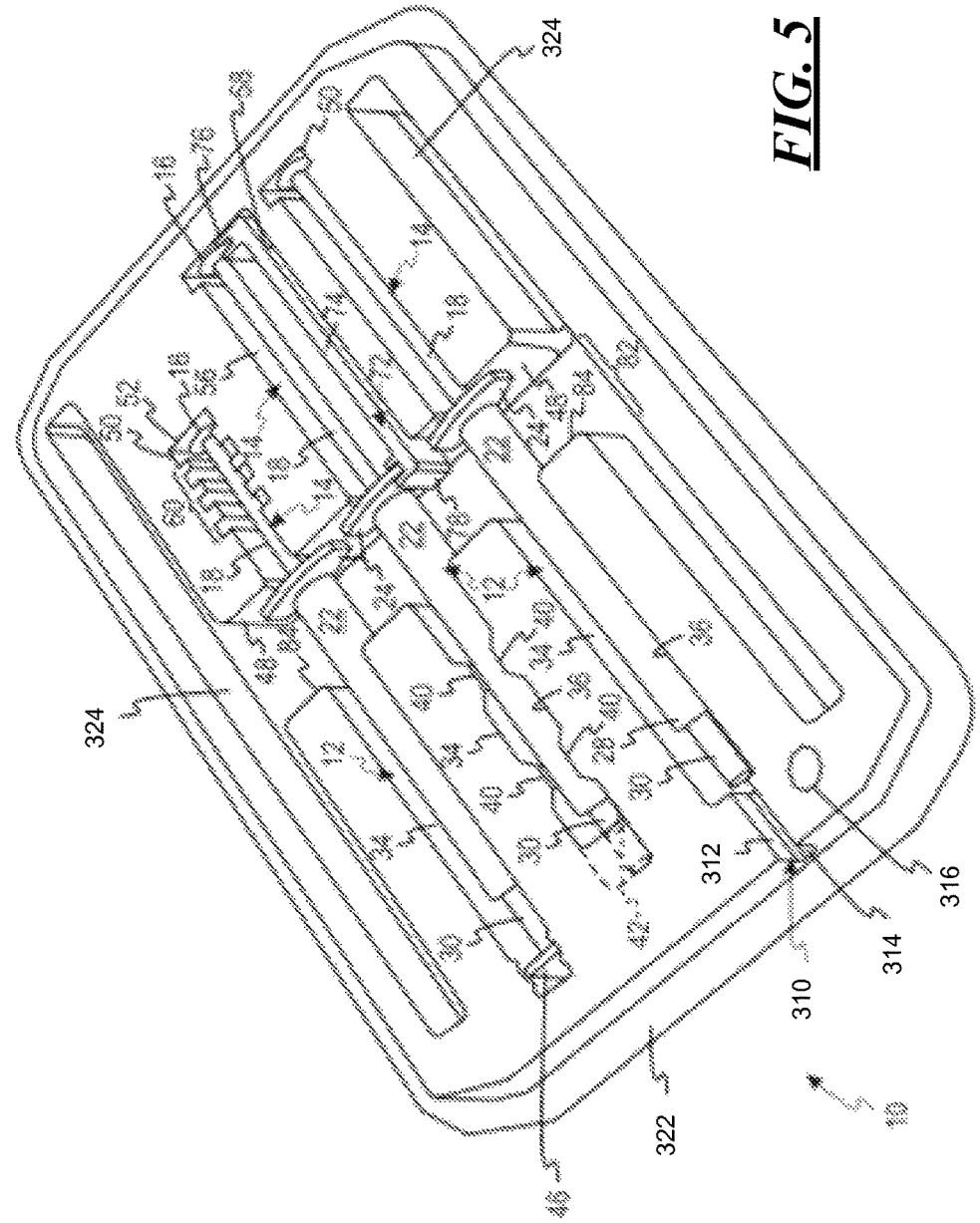

More specifically, the first segment for holding the syringe barrel 22 preferably comprises opposed sidewalls 34, 36 that are spaced to receive the barrel 22 therebetween and an end wall 38. The sidewalls 34, 36 (best seen in FIG. 3) are formed with structures to securely hold the barrel 22 of the syringe 12 in the recess 32, and past which the barrel 22 of the syringe must be forced to remove the syringe 12 from the tray 10. Preferably, the structures are projections or tabs 38 that extend beyond the faces of the sidewalls 34, 36 and into the space therebetween. As illustrated in FIG. 1-4, three tabs 40 are provided, with one tab 40 associated with sidewall 34 and two tabs 40 associated with sidewall 36. However, the number, location and configuration of the tabs 40 may be varied without departing from the scope of the disclosure. For example, as shown in FIG. 5, the sidewalls 34, 36 may be formed with two pairs of opposed elongated tabs 40. Preferably, the tabs 40 have a resilient nature, such that they deform to permit the barrel 22 of the syringe 12 to pass by, and then return to their original configuration. (It should be noted that FIGS. 5-8 illustrate multiple additional features and variations that may or may not necessarily be combined in a single embodiment of a syringe tray as described herein.) If the tray 10 is made from PETE or PETG, as described above, the tabs 40 will inherently possess the required resiliency. Preferably, the tabs provide for a snap fit to securely lock the syringe 12 into the tray 10.

Other structures may be used either in place of or in conjunction with the tabs 38 described above to securely hold and position the syringe barrel 22 in the tray 10. In a first alternative, seen in FIG. 5, the recess 32 may be formed with an aperture 42 in the end wall 38 that is sized to receive the end cap 30 of the syringe. The aperture 42 may have a shape complementary to the cross-sectional shape of the end cap, but smaller than the largest such shape for the end cap, so that the cap 30 is securely held within the aperture 42. The sidewall of the aperture may also be tapered to more securely seat and firmly grip the end cap 30. Thus, when placing a syringe 12 into a tray 10, the end cap 30 is inserted into the aperture 42, and then the barrel 22 is snapped into place between the projections 40.

Alternatively, the tray may be formed with, or be configured to receive, a clip 44 (seen in FIG. 7) that receives the end cap 30 of the syringe 12. The clip 44 is preloaded when inserting a syringe into the tray to apply a torque to the end cap 30 in a direction to screw the end cap into the luer lock 28. Similarly, the end wall 38 can be formed to receive a separately-made biasing member that engages the tip of the syringe and exerts an axial force on the barrel 22. The biasing member may comprise, for example, a spring clip 46 (as illustrated in FIG. 5), a coil spring, a resilient foam, or the like, to exert an axial force on the barrel 22 such that the finger flanges 24 are forced against lateral wall 48 in the tray opposite the end wall 38, thus positively locating the barrel 22 in the tray 10.

The syringe barrel 22 may additionally or alternatively be axially biased toward the end wall 37 by various means on the lateral wall 48 that engage the finger flanges 24. Such means may include projections or tabs integrally formed in the lateral wall 48 during the molding of the tray (similar to the tab 54, described below) or resilient means, such as springs, clips or foam, secured to the lateral wall 48 so as to engage the finger flanges 24.

Other means for securing the barrel 22 in the tray 10 may also be employed. For example, the first recess may be configured to define an aperture sized to receive the barrel of a syringe and further include spring fingers that extend into the aperture to engage the barrel to hold it securely in place, similar to a spring or push nut.

The second segment of the recess 32 is configured to receive the plunger 14 so as to prevent relative movement between the plunger 14 and the barrel 22. Specifically, motion of the plunger relative to the syringe barrel is sufficiently limited to prevent contamination of the syringe and its contents during transport of the prefilled syringes. In one alternative, the second recess preferably comprises a slot 50 for seating the thumb rest 16 of the plunger 14. The slot 50 is oriented generally transverse or perpendicularly to the slot formed by the sidewalls 34, 36, and further includes an end wall 52. The end wall 52 preferably includes a projecting tab or rib 54 that engages the top of the thumb rest 16 to positively locate the plunger 14 in the tray and limit axial movement of the plunger 14 relative to the barrel 22 of the syringe 12. Preferably, the tab 54 is deformable to account for tolerances in the fabrication of the tray 10 and the filling of the syringes. Alternatively, a separate resilient member, such as a spring or foam member (not shown), may be secured to the end wall 52 for engagement with the thumb rest 16. The second segment also preferably includes sidewalls 56, 58 that, as shown, substantially flank the length of the plunger shaft 18 extending out of the barrel 22 of the syringe 12. The sidewalls 56, 58 may optionally be formed with projections or cleats (not shown) that engage the plunger shaft 18 (similar to tabs 40) to more positively position the plunger in the tray.

Figure 6:
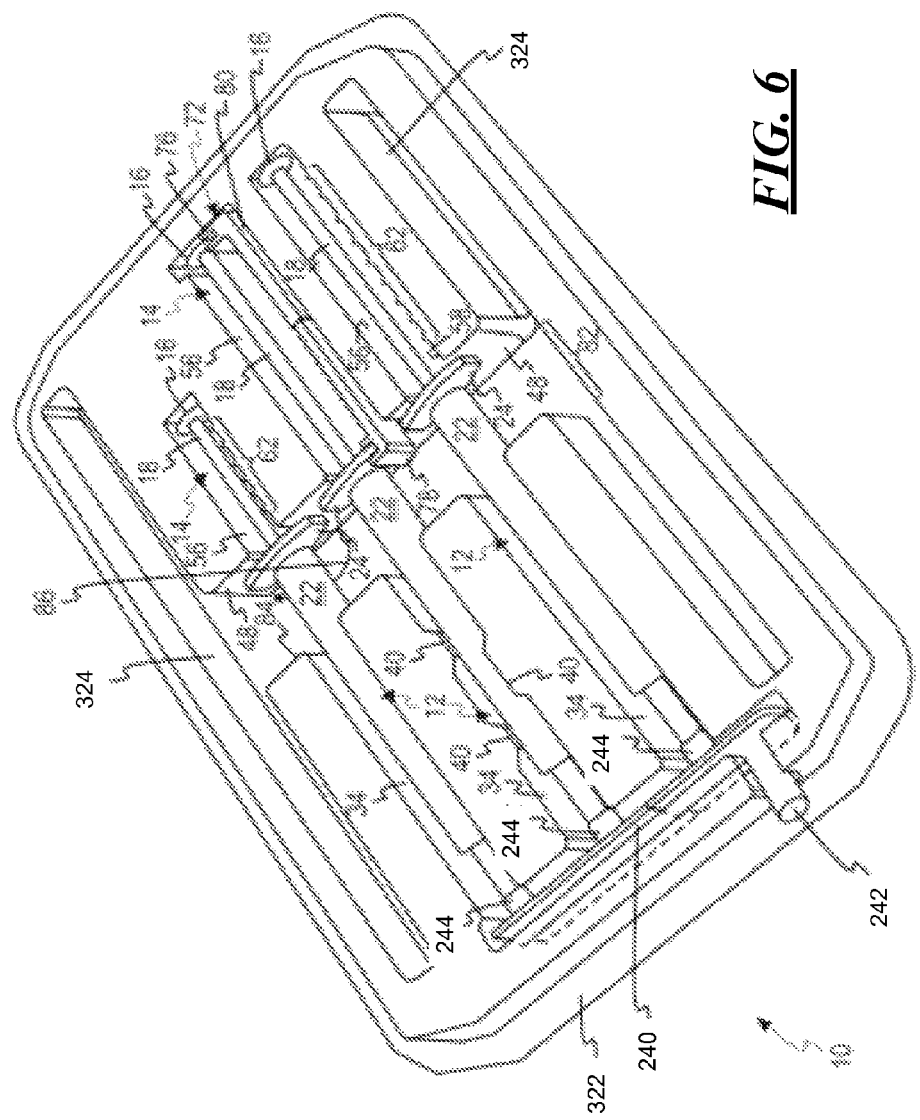

Other means may be utilized for maintaining the position of the plunger 14 relative to the barrel 22. In a first alternative, seen in FIG. 5, the second recess may be formed so as to have a plurality of transversely-oriented spaced slots 60 integrally formed therein configured to receive the thumb rest 16 of the plunger 14. Such a configuration permits the same recess 32 to be used for syringes that are prefilled with different volumes of fluid, and thus have differing positions of the plunger relative to the syringe barrel. In a further alternative, seen in FIG. 6, one or both of the sidewalls 56, 58 may be formed with a series of projecting teeth or detents 62 (as seen in FIG. 6) that engage the thumb rest 16 for various plunger settings, and thus similarly permit the second recess to accommodate syringes having multiple different thumb rest locations.

The means for securing the thumb rest of the syringe to the tray may also be formed separately from the tray and then secured thereto. For example, as shown in FIG. 7, a clip 64 may be received in the tray that has a pocket-like portion 66 that receives and captures the thumb rest and further comprises a support structure 68 configured to be received in a recess 70 in the tray 10. The support structure 68 may have a cross-like shape that is received in a T-shaped recess 70 to prevent axial and rotational movement and positively locate the clip 64 within the recess 70.

As a further alternative means separate from the tray may be utilized to maintain the relative position of the plunger to the syringe barrel. For example, a spacer bar may be employed that removably attaches to both the barrel and the plunger. More specifically, and as seen in FIG. 5, the spacer bar 72 may comprise an elongated member 74 having a structure 76 on one end that engages or captures the thumb rest 16 of the plunger 14 and a structure 78 on the other end that engages or captures the finger flanges 24 of the barrel 22. Spacers 72 of various sizes may be provided to accommodate syringes having different volumes of fluid therein. Alternatively, and with reference to FIG. 6, the elongated portion of the spacer may comprise a telescoping member 80 that is adjustable in length.

The telescoping member 80 preferably includes means for maintaining the desired spacing of the end structures. For example, one of the telescoping members could include a gear rack and the other a cooperating ratchet tooth (similar to a cable tie), although other means may occur to one skilled in the art. If a separate spacer is used, the tray 10 is configured to accommodate the spacer by, for example, increasing the spacing between the sidewalls 56, 58.

Structures such as the clip 66/structure 68 and spacer 72 may also be referred to as a tool, and in combination with the tray 10, may define a storage system. Furthermore, the tool may include not only the spacer 72, but structures of the plunger 14 as well. For example, the tool may include the thumb rest 16 and the shaft 18, whether or not those structures are attached or formed integrally (i.e., as one piece) with the remainder of the plunger 14.

Additional embodiments of a tool that may be used in combination with the tray 10 are illustrated in FIGS. 8-10a. Specifically, a first tool is illustrated in FIGS. 8 and 8a, a second tool is illustrated in FIG. 9, and a third tool is illustrated in FIGS. 10 and 10a. These tools may be used in combination with or as alternatives to the tools illustrated in FIGS. 5-7.

With respect first to a tool 90 illustrated in FIGS. 8 and 8a, it will be recognized at the tool 90 is to be combined with a syringe 92, including a barrel 94 having first and second barrel ends 96, 98, and a stopper 100 disposed between the first and second barrel ends 96, 98. The tool 90 may be used in combination with a tray 10, such as is illustrated in FIGS. 5-7, that have at least one recess in which the syringe 92 may be disposed. The tool 90 and the tray 10 may be referred to as a storage system.

The tool 90 is attached to the stopper 100 through the second barrel end 98 to limit the movement of the stopper 100 toward either one or both of the first and second barrel ends 96, 98. The tool 90 has a first end 102 attached to the stopper 100 and a second end 104 attached to the barrel 94, and in particular to a finger flange 106 (see FIG. 8a). The first end 102 of the tool 90 is selectively adjustable relative to the second end 104 to vary the distance between the first and second ends 102, 104 of the tool 90.

In particular, the tool 90 illustrated in FIGS. 8 and 8a includes an inner collar 110, an outer collar 112, and a threaded knob or wheel 114, as best seen in FIG. 8. The tool 90 also includes a shaft 116, which has a first shaft end 118 attached to the stopper 100 and a second shaft end 120, as best seen in FIG. 8a. The second shaft end 120 may have attached thereto or integral therewith a thumb rest 122. The shaft 116 may be attached to the stopper 100 such that the shaft 116 is removable, or the shaft 116 may be attached to the stopper 100 such that the shaft 116 is formed integrally with the stopper 100.

As illustrated, the inner collar 110, the outer collar 112, and the threaded wheel 114 each have a longitudinal slot 124, 126, 128. The slots 124, 126, 128 permit the shaft 116 to be inserted inside of the assembly of the inner collar 110, outer collar 112, and threaded wheel 114. As assembled, the shaft 116 is disposed with in the inner collar 110, the inner collar 110 is disposed within the outer collar 112, and the threaded wheel 114 is rotatably attached to the outer collar 112 and threadingly engages the inner collar 110.

As is also illustrated, a first inner collar end 130 abuts the second shaft end 120. More specifically, the first inner collar end 130 abuts the thumb rest 122 attached or formed at the second shaft end 120. In a similar fashion, the outer collar 112 has a first outer collar end 134 that is threadingly engaged with a second inner collar end 136. The outer collar 112 also has a second outer collar end 138 that is attached to the barrel 94. In particular, the second outer collar end 138 has a pair of slots 140 formed in the outer collar 112 to accept the finger flange 106 formed at the second end 98 of the barrel 94.

To threadingly engage the first outer collar end 132 with the second inner collar end 134, the inner collar 110 has a threaded surface 142 and the wheel 114 has an aperture 144 with an internal threaded surface 146. See FIG. 8. The engagement of the threaded surface 142 with the threaded surface 146 defines the threaded engagement of the inner collar 110 with the outer collar 112. The wheel 114 has a slot 148 in which a rim 150 of the outer collar 112 is received to secure the wheel 114 to the outer collar 112 such that the inner collar 110 and the wheel 114 may rotate relative to the outer collar 112, but the wheel 114 is not permitted to move axially relative to the inner collar 110 or the outer collar 112. On the other hand, the inner collar 110 is free to move axially (translate) relative to the outer collar 112. In this fashion, rotation of the wheel 114 clauses rotation and axial movement (translation) of the inner collar 110 relative to the outer collar 112.

This axial movement or translation of the inner collar 110 causes movement of the thumb rest 122 relative to the barrel 94, which causes relative motion between the stopper 100 and the barrel 94. This motion between the stopper 100 and barrel 94 is selectable in that the user will be aware of the distance that the stopper 100 moves relative to the barrel 94 for each rotation of the wheel 114. Moreover, by providing a detent, lock or latch, the wheel 114 may be used to fix a relative distance between the stopper 100 and the first end 96 of the barrel 94. As such, the tool 90 may be used to provide a selectable and securable (or fixed) spacing between the stopper 100 and the first end 96 of the barrel 94.

A second tool 160 is illustrated in FIG. 9 in combination with a syringe 92 having a barrel 94 with first and second ends 96, 98, a stopper 100, and finger flange 106. The second tool 160 includes a shaft 162 and a wheel 164. As such, the tool 160 bears certain similarities to the tool 90. The tool 160 also includes a lock or latch that secures the wheel 164 relative to the shaft 162 such as was mentioned with reference to the tool 90.

The shaft 162 has a first shaft end 166 attached to the stopper 100 and a second shaft end 168, which shaft end 168 may be formed with a thumb rest 170. The shaft 162 has a threaded surface 172 formed at least along a section of the shaft 162 between the first end 166 and the second end 168. According to certain embodiments, the shaft may be threaded along the entirety of the shaft 162 between the first and second ends 166, 168.

The wheel 164 has an aperture 174 formed therein. The aperture 174 has an internal threaded surface 176, which internal threaded surface threadingly engages the threaded surface 172 of the shaft 162 when the shaft 162 is disposed through the aperture or passage 174. The wheel 164 also has a surface 178 that abuts a rim 180 formed at the second end 98 of the barrel 94 of the syringe 92 (such as may be formed or defined by a finger flange 106).

The wheel 164 is free to rotate relative to the barrel 94 and the shaft 162. The shaft 162 may be relatively unable to rotate relative to the barrel 94 because of the interaction between the stopper 100 and the barrel 94, or at least it may be said that the interaction between the stopper 100 and the barrel 94 resists rotation caused by operation of the wheel 164. Consequently, rotation of the wheel 164 moves the wheel axially along the shaft 162, or at least that section of the shaft 162 between the first end 166 and the second end 168 that is threaded.

In particular, the wheel 164 may be rotated relative to the shaft 162 so as to position the wheel 164 spaced from the finger flanges 106 of the syringe 92 in the direction of the end 168. The axial distance between the surface 178 and the finger flanges 106 (or more particularly the rim 180) will define a distance through which the tool 160 and attached stopper 100 may move in the direction of the first end 96 of the barrel 94. Consequently, if the wheel 164 abuts the second end 98 of the barrel 94, the stopper 100 is unable to move in the direction of the first end 96 of the barrel 94. If the wheel 164 is spaced from the second end 98 of the barrel 94, the stopper 100 may move in the direction of the first end 96 of the barrel 94 the same distance as the surface 178 is spaced from the rim 180.

According to this tool 160, not only made the stopper 100 be positioned in a selectable and securable location within the barrel 94 (at least in the direction of the first end 96 of the barrel 94), the tool 160 may be used to select a specific dose to be delivered from the syringe 92. That is, if the wheel 164 is spaced from the second end 98 of the barrel 94, such that the stopper may move in the direction of the first end 96 in the same distance as the surface 178 is spaced from the rim 180, this distance can be correlated to an amount of product to be ejected from the first end 96 of the barrel 94. Consequently, by moving the wheel 164 along the shaft 162, the amount of product to be ejected from the barrel may be selectively controlled.

A further tool 200 is illustrated in FIGS. 10 and 10a in combination with a syringe 92 having a barrel 94 with first and second ends 96, 98, a stopper 100, and finger flange 106. This tool 200 may be particularly useful relative to the tray 10 illustrated in FIGS. 1-4, insofar as the tool 200 may be used to select and secure (or fix) a particular distance between the stopper 180 and a surface of the recess of the tray 10. See FIG. 10A. Specifically, the tool 200 may include a shaft 202 having first and second shaft sections 204, 206.

The first shaft section 204 may have a first end 208 that is attached to the stopper 100. The first shaft section 204 may also have a second end 210 that threadingly engages a first end 212 of the second shaft section 206. The second shaft section 206, in turn, may abut a surface of the at least one recess of the tray 10 as illustrated in FIG. 10a. According to one embodiment, a second end 214 of the second section 206 may abut the surface of the recess of the tray 10. In fact, the second end 214 of the second shaft section 206 may have a thumb rest 216 attached or formed integrally therewith that may be received within a slot transverse to the recess such that the thumb rest 216 is secured relative to the tray 10, at least with respect to the axial motion of the thumb rest 216 in the direction of the first and second ends 96, 98 of the barrel 94.

To threadingly engage the second end 210 of the first section 204 with the first end 212 of the second section 206, the first section 204 may have a threaded surface 218 along at least a region of the first shaft section 204 adjacent the second end 210. The first end 212 of the second shaft section 206 may have a hollow collar 220 with an internal thread that engages the threaded surface 218 of the first shaft section 204. By rotating the second shaft section 206 relative to the first shaft section 204, the axial distance between the stopper 100 and the rest 216 may be varied. By providing a relatively stiff connection between the first and second shaft sections 204, 206, the axial distance between the stopper 100 and the rest 216 may be secured or fixed. As a consequence, the tool 200 permits a specific axial distance between the stopper 100 and the thumb rest 216 to be selected and secured.

As such, the tool 200 permits the barrel 94 of the syringe 92 to be filled to any volume within a wide range of volumes and then the sections 204, 206 adjusted such that the distance between the stopper 100 and the thumb rest 216 permits the thumb rest 216 to abut a surface of the recess of the tray 10 such that movement of the stopper 100 is limited, and even potentially completely restricted. Consequently, the tool 200 permits syringes 92 to be filled with various volumes, and yet to use a common tray that admits only syringes 92 with a particular distance between the finger flange 106 and the thumb rest 216. This is advantageous in that it is no longer a requirement that the tray 10 be configured to the syringe 92, as the syringe 92 can be adapted through the use of the tool 200 to use a common or standardized tray 10.

Returning now to FIG. 1, it will be recognized that the third segment of the tray comprises a relieved portion 230 that provides access to the syringe barrel 22 to facilitate removal of the syringe 12 from the tray 10. As illustrated, the relieved portion 230 is located intermediate the first segment and second segment and is defined by opposed sidewalls 48, 232. However, the third segment could be located within the first segment. As described above and seen in FIG. 1, sidewall 48 is preferably positioned so as to abut the finger flanges 24 of the barrel 22 when a syringe 12 is held in the recess 32, with the tip of the needle sheath 30 either contacting the end wall 38 of the first segment or otherwise being engaged or secured in the tray as described above. As such, the barrel 22 is unable to move axially within the tray 10. Sidewall 232 is spaced from sidewall 48 a distance sufficient to permit finger access to the barrel. Optionally, the relieved portion 230 may have a depth sufficient to permit rotation of the syringe barrel 22 about its longitudinal axis (as shown by the arrow 234 in FIG. 6). To this end, the depth of the relieved portion 210 is preferably greater than the combined width of the finger flanges 24 and diameter of the barrel 22.

In keeping with another aspect of the disclosure, the tray may include additional features that provide greater functionality. For example, as seen in FIG. 6, the tray may be configured to receive a separately made manifold 240 that interconnects in fluid communication each of the syringes 12 to be held in the tray 10. The manifold 240 includes an inlet/outlet port 242 and a series of junction ports 244, one for each syringe, configured so that the barrel 22 of each syringe may be secured to the manifold 240 and to provide fluid communication through the manifold 240 to the interior of the syringe barrel 22. The manifold 240 may be utilized to facilitate the simultaneous filling of the syringes 12 and/or to sequence the use of the syringes 12 during administration of their contents. After filling the syringes 12 by introducing fluid through the inlet/outlet port 242 of the manifold 240, the port of the manifold 240 is sealed by, for example, a separate cap, a self-sealing gasket, or other means as may occur to a person skilled in the art.

The manifold may be use for other purposes as well. For example, if the position of the stopper is held substantially fixed (i.e., with little possibility for motion relative to either end of the barrel), then the constituents of the product contained within the syringe may separate or settle during storage, for example where the product includes cells of higher specific gravity suspended in a fluid of lower specific gravity. It may be desirable to provide a mechanism that permits the separate components of the product contained within the barrel of the syringe to mix to maintain the cells suspended in solution. Such a mechanism may limit or eliminate the need to take other steps to re-suspend the cells after storage/shipment and prior to administration, which resuspension may be important to ensuring that a homogeneous mix of cells is provided for consistent cell volume per activation and accurate and consistent dose volumes. The manifold may be provided with such a mechanism between the inlet/outlet port and the junction ports.

Figure 11:
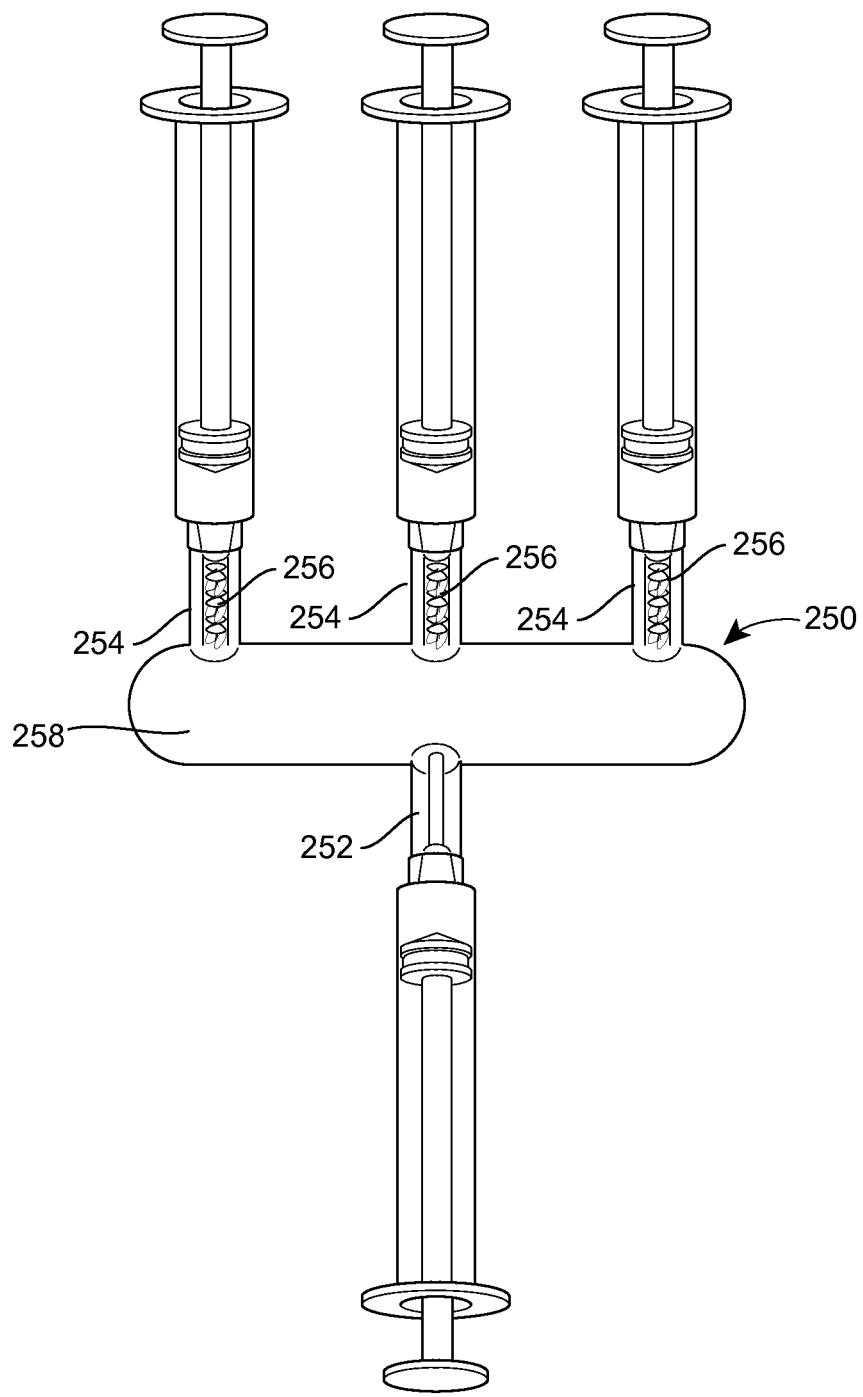
FIG. 11 is a perspective view of a manifold that may be used as an alternative to the manifold illustrated in FIG. 6.

In particular, FIG. 11 illustrates a manifold 250 similar to that illustrated in FIG. 6, in that the manifold 250 includes an inlet/outlet port 252 and at least one junction port 254 (as illustrated, the manifold 250 includes three junction portions 254). A first syringe may be attached to the inlet/outlet port 252 as illustrated, and a syringe may be attached to each of the three junction ports 254. The syringes attached to each of the three junction ports 254 may be used to transfer a product into the first syringe.

As mentioned above, it is possible for one of the constituents of the product stored in each of the syringes attached to the junction ports 254 to settle out of solution. This could cause an issue with the administration of the product, as also mentioned above. Therefore, a static mixer 256 is disposed in each of the junction ports 254, such that the product passing through each of the junction ports 254 on its way to the inlet/outlet port 252 passes through a mixer 256. As a consequence, the constituents are mixed with each other after they are ejected from the syringes attached to the junction ports 254 before reaching the inlet/outlet port 252. The mixer 256 may be in the form of one or more baffles or protrusions that define a tortuous path as illustrated; alternatively, the mixer 256 may be in the form of a disc of a porous material having tortuous, interconnecting passages, or a system of meshes or membranes to achieve a similar result. The manifold 250 may also include an intermediate container or chamber 258 to receive the material that has passed through the mixer 256.

As an alternative to the embodiment as illustrated, a mixer may be disposed with a tip of the syringe, instead of within the junction ports 254.

Figure 12:
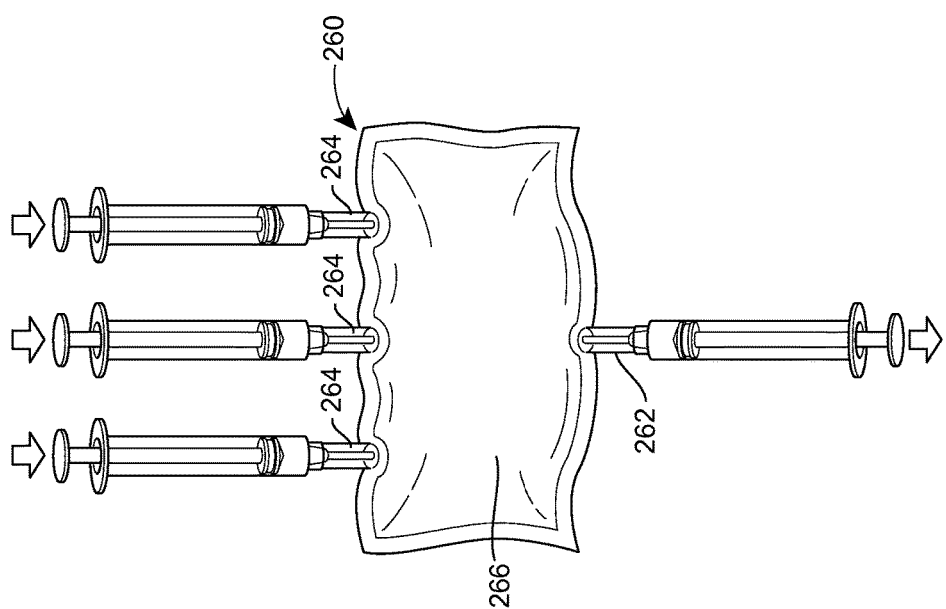
FIG. 12 is a perspective view of a manifold that may be used in combination with or as an alternative to the manifolds illustrated in FIGS. 6 and 11.

In the alternative or in combination with static mixers disposed in one or more of the junction ports, the manifold may be provided with another mechanism for improving the homogeneity of the product exiting through the inlet/outlet port. As illustrated in FIG. 12, a manifold 260 is provided with an inlet/outlet port 262 and junction ports 264. The manifold 260 also includes a flexible container 266, such as in the form of a flexible bag, that is connected to and in fluid communication with the inlet/outlet port 262 and the junction ports 264. A syringe may be attached to any one or all of the junction ports 264, and product may be ejected from the syringe(s) into the flexible container 266 through the junction ports 264, after which the container 266 may be manipulated (e.g., kneaded) to encourage mixing of the product ejected from the syringes into the container 266. After the product is mixed, it may be drawn into a syringe attached to the inlet/outlet port 262.

Figure 13:
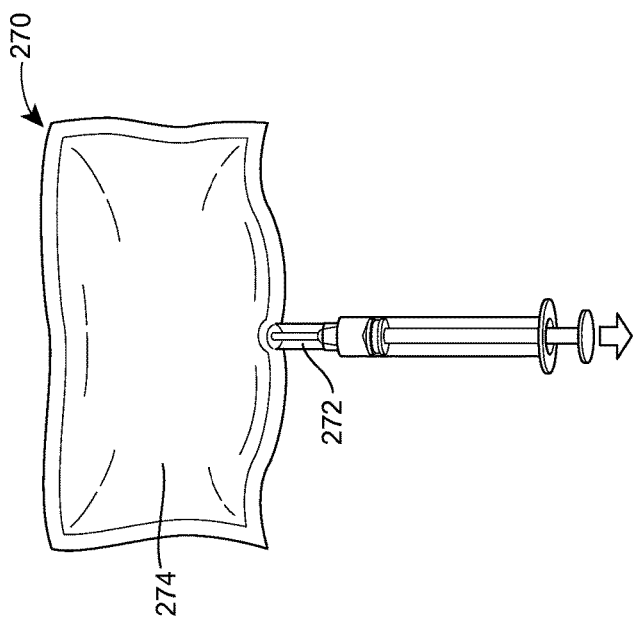
FIG. 13 is a perspective view of a mixing system that may be used as alternative to the manifolds illustrated in FIGS. 6, 11 and 12.

FIG. 13 illustrates a mixing system 270 that is similar to the manifold 260 illustrated in FIG. 12. In particular, the mixing system 270 includes an inlet/outlet port 272 attached to a flexible container 274. A syringe may be attached to the port 272, and product to be mixed ejected from the syringe through the port 272 into the container 274. The container 274 may then be manipulated (e.g., kneaded) to encourage mixing of the product, after which the product may be drawn from the container 274 into a syringe for administration to the patient.

Figure 14:
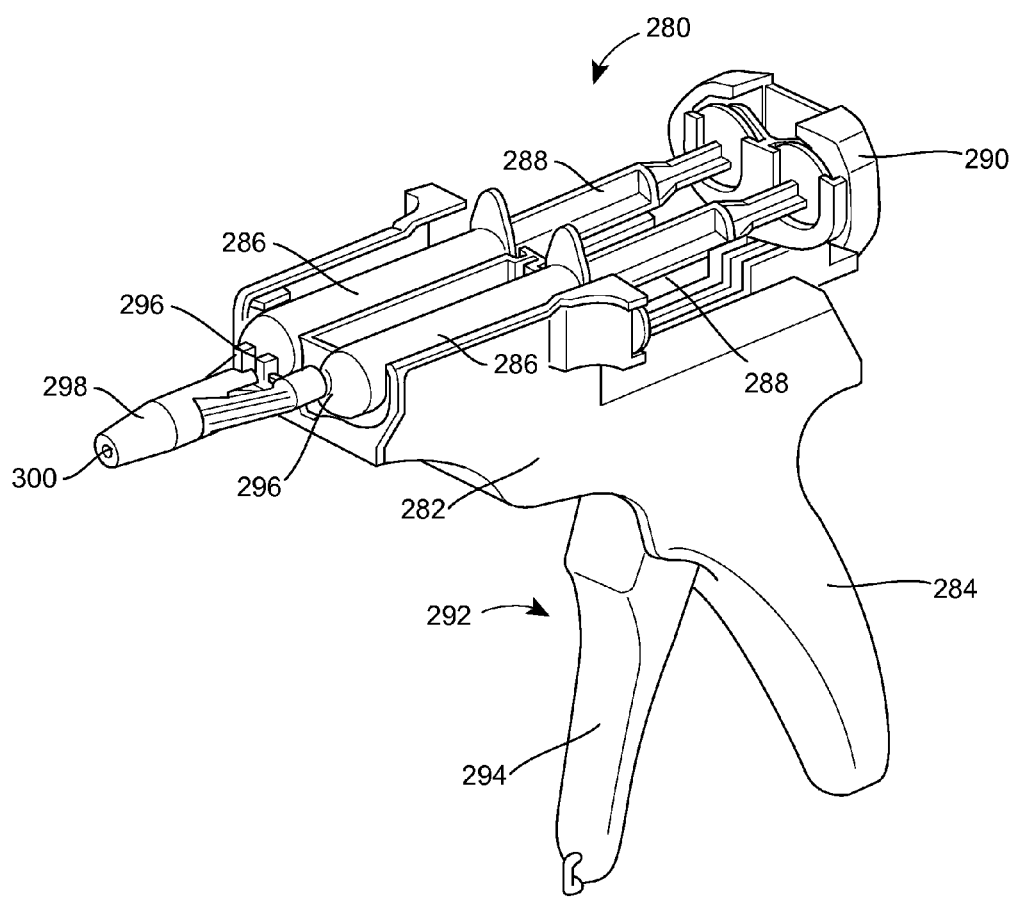
FIG. 14 is a perspective view of a mixing system that may be used as alternative to the manifolds illustrated in FIGS. 6, 11 and 12 or the mixing system illustrated in FIG. 13.

FIG. 14 shows an alternate mixing system, indicated generally at 280. Such a system is shown having a conventional gun-type applicator construction, although other constructions are also possible. The system 280 generally defines a body 282 and a handle 284. The body 282 defines respective cavities for receiving product-filled syringes 286 having respective plungers 288 extending therefrom. While the system 280 has been illustrated with two product-filled syringes 286, the system 280 may be designed for use with only one syringe 286 or more than two syringes 286.

Each proximal end of the plunger 288 is received by a pusher member 290. An actuating member, generally indicated at 292, is preferably operatively associated with the pusher member 290. The actuating member 292 includes a lever 294 which may be distally located and pivotally movable relative to the handle 284. The lever 294 may be operatively connected to the pusher member 290 by a drive mechanism shown and described in U.S. Pat. No. 6,585,696, which is assigned to Baxter International Inc., the assignee of the present application, and which patent is incorporated herein by reference. Accordingly, such mechanism need not be described further.

Each syringe 286 has a tip 296 that is received in an adapter 298 that has an outlet 300. The tips 296 of the syringes 286 are in fluid communication with the outlet 300 via one or more static mixers disposed in the adapter 298. For example each tip 296 may connect to a separate passage, which passages may meet and join at a junction prior to the outlet 300. One or more static mixers may be disposed in each of the separate passages prior to the junction, one or more static mixers may be disposed after the junction but prior to the outlet 300, or static mixers may be disposed in each of the separate passages and after the junction but prior to the outlet 300.

In operation, the lever 294 may be pivoted in a direction towards the handle 284 for actuation. Movement of the lever 294 causes movement of the plungers 288 in the direction of the tips 296 of the syringes 286, causing the product contained in the syringes to be ejected into the adapter 298. Movement of the product through the adapter 298, and in particular the static mixers, causes the constituents of the product to mix, enhancing the homogeneity of the product prior to its administration through the outlet 300 to the patient.

As a further additional feature, the tray may be provided with means that facilitate the removal of the end cap 30 from each syringe 12 which may have been over tightened after filling the syringe 12. Accordingly, the tray 10 may include a structure 310 (as illustrated in FIG. 5) which serves as a wrench for securely holding the end cap. In one alternative, the wrench structure 310 may comprise a slot defined by sidewalls 312, 314. After removing the syringe 12 from the tray, the end cap 30 is wedged between the sidewalls 312, 314. The sidewalls 312, 314 are spaced so that they tightly grip the cap 30, thus permitting the barrel 22 to be twisted relative to the cap 30 to unscrew the cap from the syringe 12. In a second alternative, the syringe tray 10 may be formed with an aperture 316 having a shape complementary to the cross-sectional shape of the end cap 30, but of a size smaller than the largest cross-sectional shape, so that the end cap 30 may be inserted into the aperture 316 to firmly grip the cap 30 and permit its unscrewing from the syringe by the application of torque to the syringe barrel 22.

The prefilled syringes 12 are preferably placed in tray 10 in an aseptic manner. The combination is then preferably sterilized and a cover is preferably sealed to the tray 10 so as to overlie the syringes. Preferably, the cover may be made of plastic material, such as Tyvek®, that is heat sealed to the top surface of the tray. The tray is then preferably placed in an over-pouch to maintain sterility until the time of use. Double bagging the tray is preferred, with the outer pouch being resealable.

In accordance with another aspect of the disclosure, the tray 10 is configured so as to reduce the likelihood that it could puncture an over-pouch, and thus increase the contamination potential of the syringes. To this end, the tray 10 preferably has no sharp edges, and the corners (such as corners 320) are rounded or beveled. The tray 10 may also be provided with an outer edge in the form of a flange 322 that helps to reduce the angle at which the inner surface of the over-pouch engages the corners 320, thus further reducing the likelihood of puncture. As illustrated, the tray 10 is also formed with a pair of elongated parallel supports 324 that serve to increase the rigidity of the tray and provide a stable base for the tray when placed on a flat surface.

Figure 15:
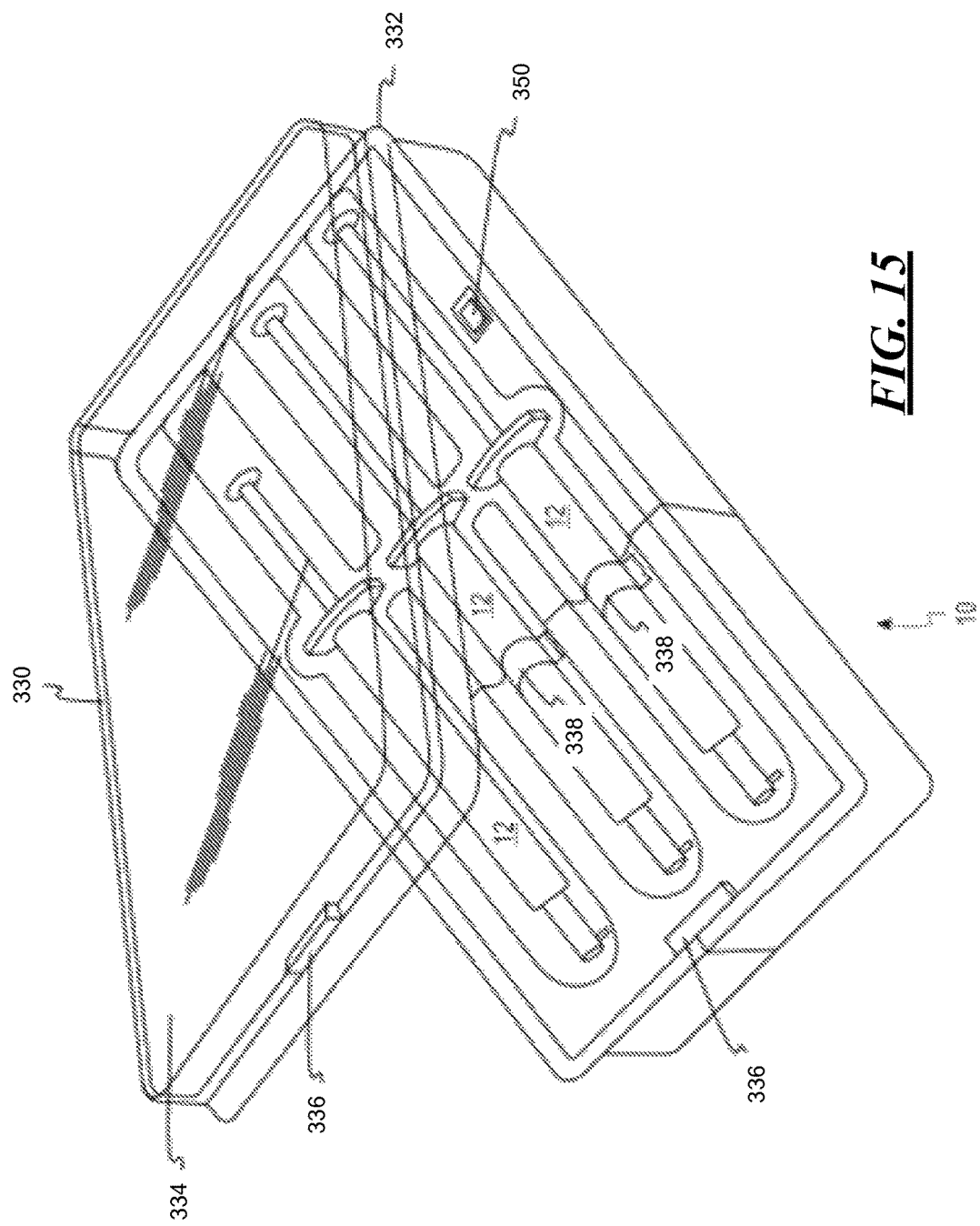
FIGS. 15 and 16 show a syringe tray in combination with further packaging including a cover or closure member.

In keeping with another aspect of the disclosure, the syringe tray 10 may be part of a housing assemblage having a reclosable cover to provide a more durable and protective enclosure for the syringes held in the tray. With reference to FIG. 15, the tray 10 is provided with a cover 330 and is preferably formed integrally with the tray 10, with a living hinge 332, or other hinge structure, connecting the two. The cover 330 preferably has a depth sufficient to receive a resilient/expandable insert or void filler 334, comprising, for example, an encapsulated foam material, that presses against the syringes 12 held in the tray 10 upon closure of the cover 330 to more securely hold the syringes 12 in place and provide additional protection.

The cover 330 and tray 10 are preferably provided with a latch or lock structure 336 (as illustrated in FIG. 8) to secure the cover in the closed position. For example, the latch or lock 336 may comprise a magnet in combination with another magnetic or magnetizable material in opposed relationship on the tray and cover. Alternatively, the cover and tray may be provided with interfitting, complementarily-shaped projections and recesses (not shown) that frictionally engage each other upon closure of the cover 330.

In another aspect of the disclosure, the barrels of the syringes may be provided with a mark indicating the position of the piston within the barrel at the time the filled syringe is secured in the tray. When the syringe tray is unloaded prior to use, the mark provides a visual indication as to whether the piston has moved during shipment. As illustrated in FIG. 15, the barrel marking may comprise a length of tape 338 applied to the barrel, although other means of marking the syringe barrel and/or the tray to indicate the position of the piston may be employed.

Figure 16:
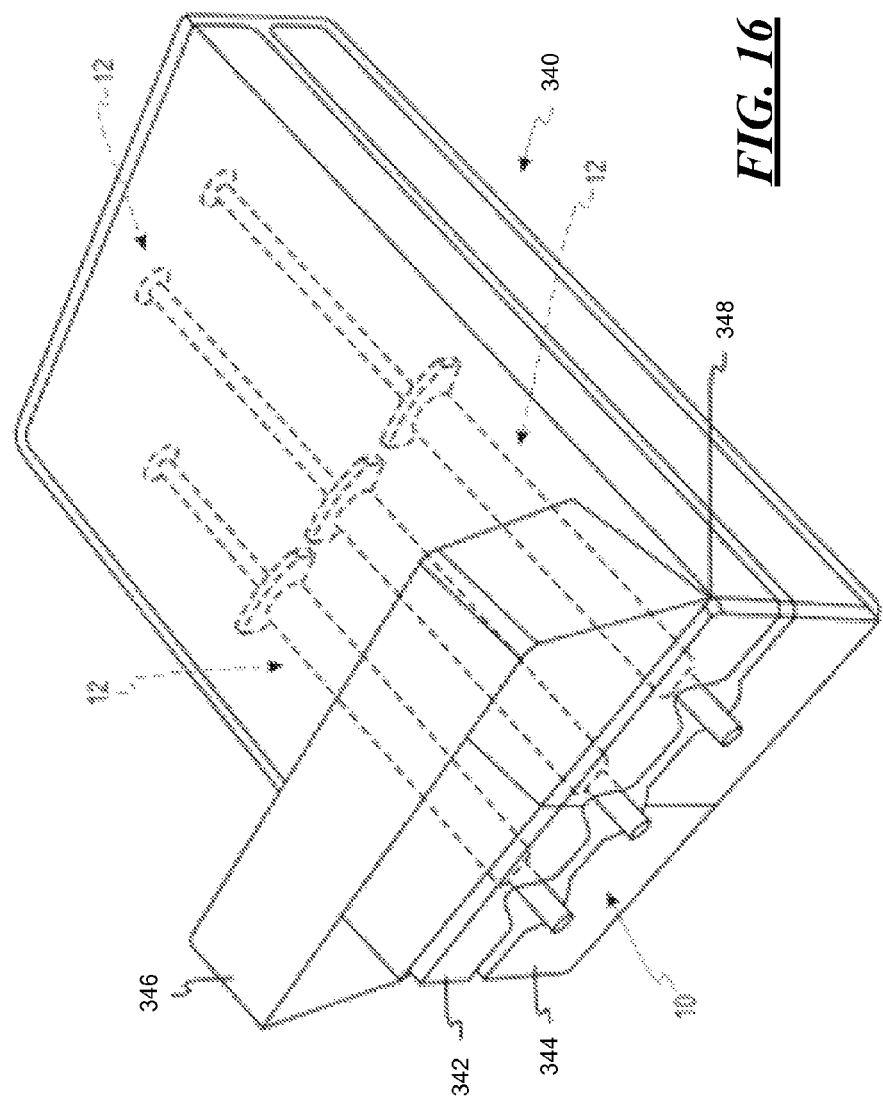

Alternatively, as seen in FIG. 16, a tray 10 loaded with syringes 12 may be received in a separate box-like container 340 open on one end, such that the filled tray 10 is slided into the container 340. As illustrated, the tray comprises deformable members 342, 344, made of a material such as the encapsulated foam described above, for securely positioning the syringes 12 within the container 340, although the container 340 may be configured to receive any of the syringe trays described above. The container 340 is preferably provided with a closure 346 for the open end. In the illustrated embodiment, the closure is hingedly attached (at 348) to the remainder of the container 340, although a separate closure that slides over the open end of the container may be used. Preferably, the closure 346 and container 340 include a latch or other means (such as the latches described above) for releasably securing the closure 346 to the container 340 in the closed position to secure the syringe tray 10 therein.

As seen in FIG. 15, the syringe tray may also include a sensor 350 affixed thereto that measures and stores data as to the conditions to which the syringes 12 are subjected during shipment and prior to use that could potentially affect the efficacy of the substances administered by the syringes. Such data could include information as to vibration, temperature, and/or humidity.

As was the case with reference to the embodiments of FIGS. 1-7a, the prefilled syringes 12 are preferably placed in tray 10 in an aseptic manner. The combination is then preferably sterilized and a cover is preferably sealed to the tray 10 so as to overlie the syringes. Preferably, the cover may be made of plastic material, such as Tyvek®, that is heat sealed to the top surface of the tray. The tray is then preferably placed in an over-pouch to maintain sterility until the time of use. Double bagging the tray is preferred, with the outer pouch being resealable. Consequently, similar safety measures as were provided relative to the embodiments of FIGS. 1-7a may be provided relative to other embodiments as well.

The housing assemblage of which the syringe tray 10 is part need not be provided simply to further enclose or protect the tray 10 or the syringes 12 disposed in the tray 10. The housing assemblage or additional packaging may be configured to provide to move the tray 10 (and thus the syringes 12 disposed in the tray 10) during shipment and/or storage to encourage mixing within the product, and to thus encourage the homogeneity of the product when it is time to administer the product.

FIGS. 17-22 illustrate a number of storage systems that include a syringe tray and additional packaging configured to encourage mixing during shipment and/or storage. The storage systems each include a tray having at least one recess in which at least one syringe is disposed, the syringe including a barrel with first and second barrel ends, and the stopper fixedly disposed between the first and second barrel ends. The storage systems also include a motion generator attached externally to the at least one syringe. The motion generator may be one of at least a vibration generator and a rotating frame.

Figure 17:
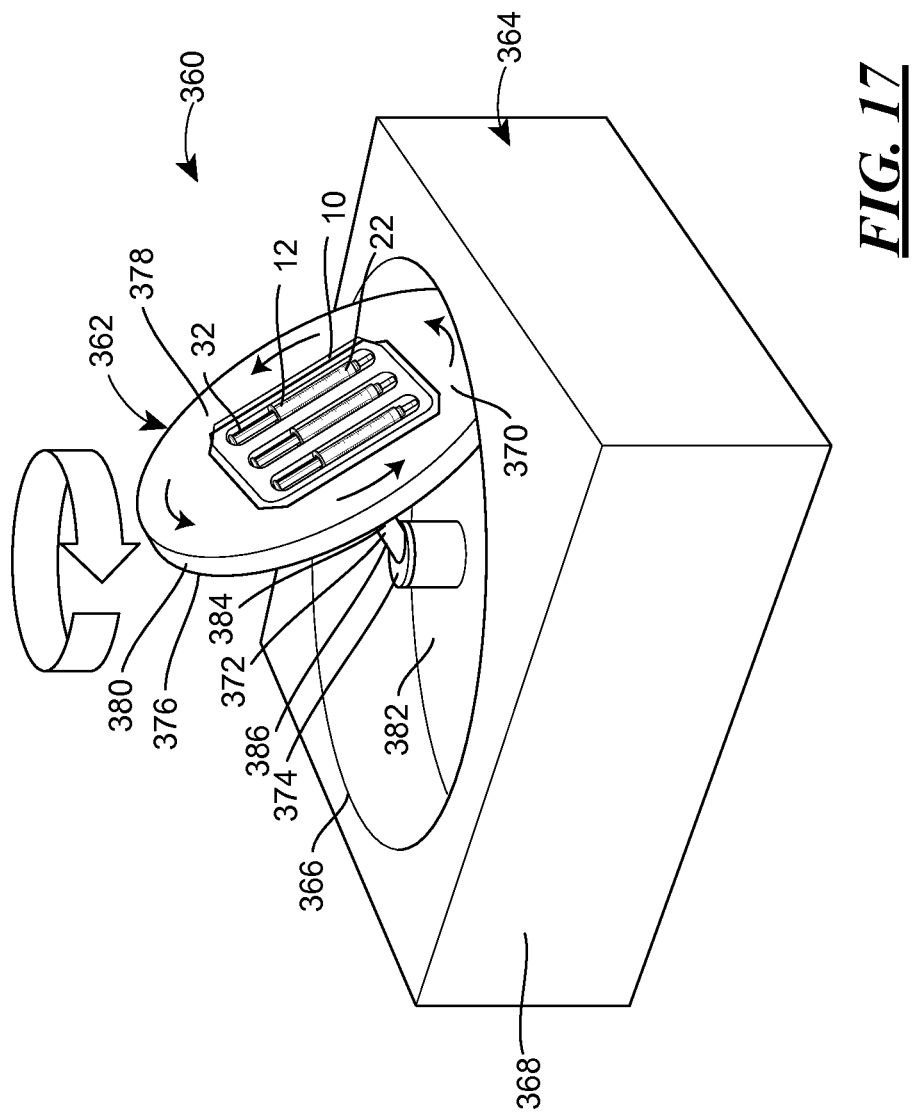
FIG. 17 is a perspective view of a syringe tray in combination with further packaging including a rotating table.
Figure 18:
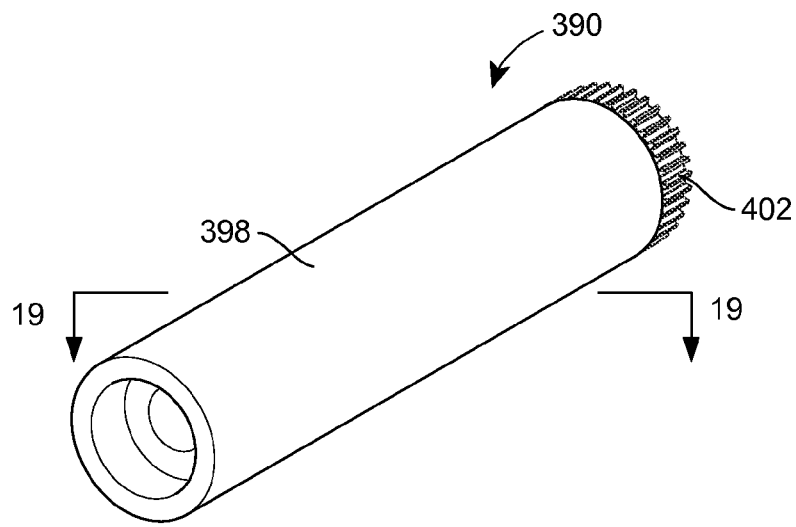
FIG. 18 is a perspective view of a packaging system including a rotating table for use with a syringe tray as illustrate illustrated in FIG. 19.

FIG. 17 illustrates a storage system 360 that includes a tray 10 similar to those described above in which syringes 12 are disposed in recesses 32, each syringe 12 including a barrel 22 with first and second barrel ends and a stopper fixedly disposed between the first and second barrel ends for example through the use of the tool or other feature of the tray 10. The storage system 360 also includes a rotating frame 362 to which the tray 10 is attached. The storage system 360 further includes outer packaging 364 that surrounds the assembly of the tray 10 and the rotating frame 362. In particular, the outer packaging 364 includes a recess 366 in which the assembly of the tray 10 in the rotating frame 362 is disposed. While only a lower section 368 of the outer packaging 364 is illustrated in FIG. 17, it will be understood that an upper section of similar shape and structure would also be provided to fully enclose the assembly of the tray 10 and rotating frame 362.

The rotating frame 362 includes a circular table 370, an arm 372 and a pivot or pivot joint 374. The circular table 370 has first and second opposing faces 376, 378 bounded by a circular rim 380. The circular rim 380 rests on a surface 382 of the recess 366. The arm 372 has a first end 384 attached to the face 376 of the table 370, and a second end 386 attached to the pivot joint 374. As illustrated, the length of the arm 372 is selected such that the table 370 is position with its faces 376, 378 disposed in an inclined plane relative to the surface 382, so as to assure that the syringes will be rotating in two planes relative to the vertical. The tray 10 is attached to the second face 378 of the circular table 370.

During shipment, the circular table 370 is free to move in a pattern about the pivot 374 with the rim 380 contacting the surface 382. This causes the tray 10, and in particular the syringes 12 disposed in the frame 10, to change their orientation relative to the outer packaging 364. As a consequence, it is believed that the product disposed within the syringes 12 also changes its orientation, leading to mixing of the mixing of the constituents of the product within the syringe 12 during shipment.

An alternative storage system 390 is illustrated in FIGS. 18-20c. According to the storage system 390, a rotating frame 392 is provided along with specially-designed trays 394 with syringes 396 disposed therein. The rotating frame 392 and the trays 394 are enclosed within an outer packaging or housing 398. Similar to the storage system 360, the rotating frame 392 of the storage system 390 causes motion of the tray 394, and thus motion of the syringe 396 disposed within a recess of the tray 394.

The rotating frame 392 includes a shaft 400 and a drive 402.

The shaft 400 is disposed within the housing 398, and has an outer shaft surface 404 that faces an inner housing surface 406. The housing 398 and the shaft 400 are both preferably cylindrical in shape, with the central longitudinal axis of the shaft 400 lying along the central longitudinal axis of the housing 398. The tray 394 is also cylindrical in shape, and one or more of the trays 394 may be disposed between the inner housing surface 406 of the housing 398 and the outer shaft surface 404 of the shaft 400 with the tray 394 abutting the inner housing surface 406 and the outer shaft surface 404. In fact, as illustrated, the trays 394, outer packaging 398, and shaft 400 may have teeth disposed thereon which mesh together, the trays 394, outer packaging 398, and shaft 400 defining a planetary gear system. Rotation of the shaft 400 may cause rotation of the trays 394, and rotation of the syringes 396 disposed therein. Rotation of the syringes 396 is believed to encourage mixing of the constituents of the product disposed within the syringes 396.

Figure 19:
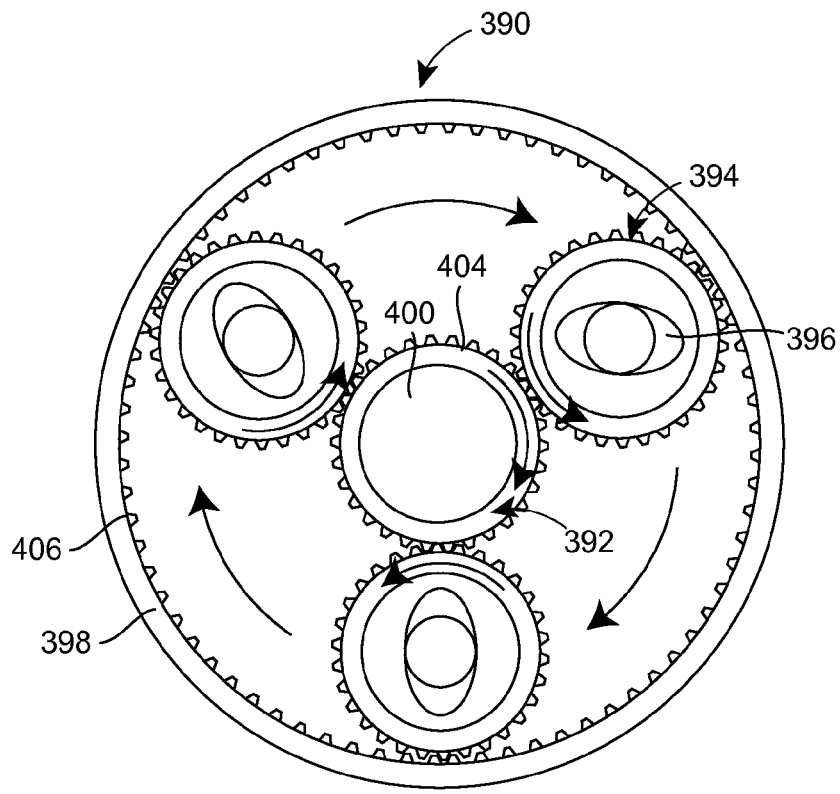
FIG. 19 is a cross-sectional view of the packaging system of FIG. 18 taken along line 19-19.
Figure 20A:
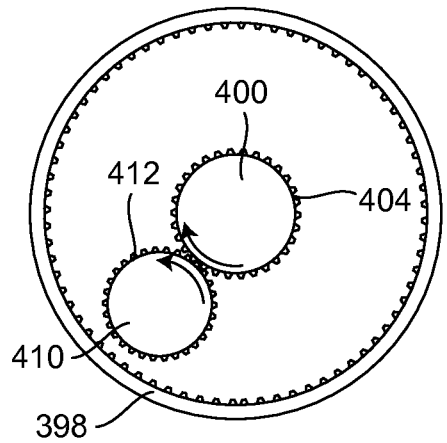
FIGS. 20a-20c are views of various drives to be used in combination with the packaging system of FIGS. 18 and 19.
Figure 20B:
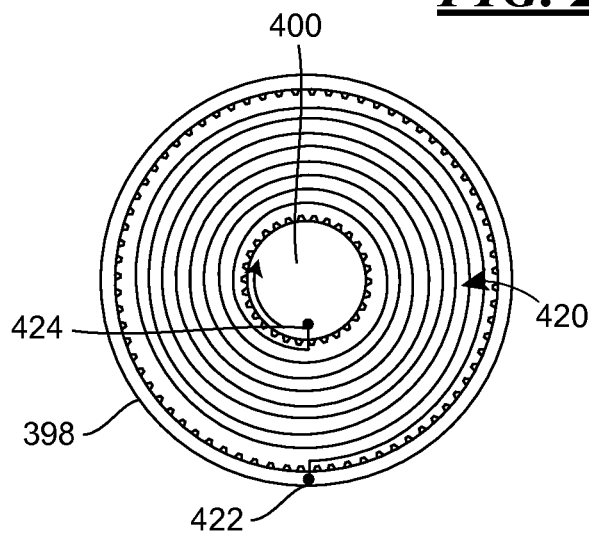
Figure 20C:
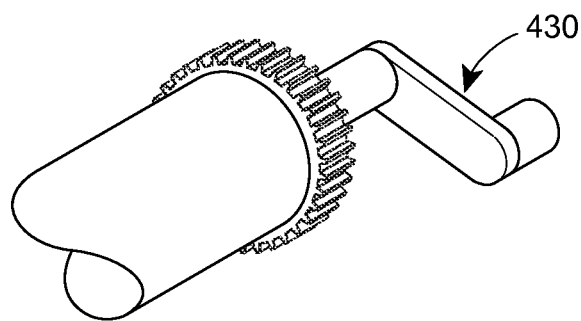

The drive 402 may be disposed in the housing 398, or may be attached at one end of the housing 398 (see FIG. 19). As illustrated in FIGS. 20a-20c, the drive 402 may be any of a number of different mechanisms. For example, as illustrated in FIG. 20a, the drive 402 may include a motor 410 having a surface 412 that cooperates with the outer shaft surface 404 to cause rotation of the shaft 400 about its central longitudinal axis. As illustrated in FIG. 20b, the drive 402 may include a spring 420 (e.g., a torsion spring) having a first end 422 attached to the housing 398 and a second end 424 attached to the shaft 400, which spring may be hand-wound, for example, to provide a rotational force to the shaft 400. As illustrated in FIG. 20c, the drive 402 may include a hand crank 430 that is directly or indirectly attached to the shaft 400, rotation of the hand crank 430 resulting in rotation of the shaft 400 about its central longitudinal axis.

Figure 21:
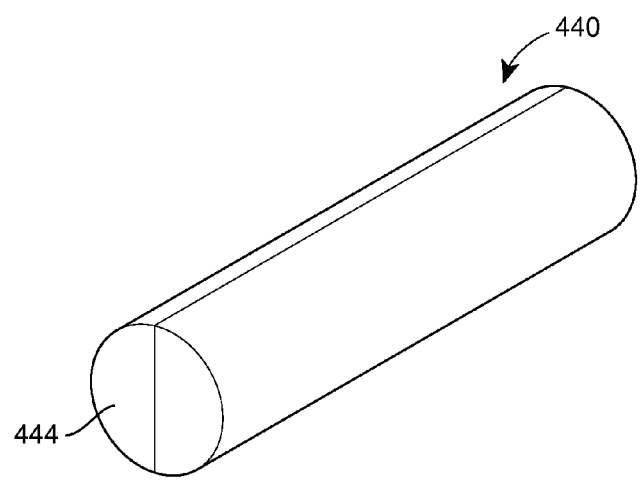
FIG. 21 is a perspective view of a syringe tray that may be used in combination with or as an alternative to the preceding syringe trays.
Figure 22:
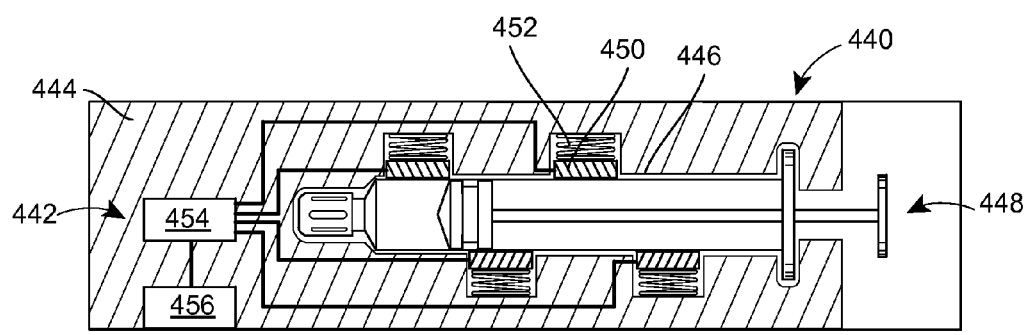
FIG. 22 is a cross-sectional view of the syringe tray of FIG. 21.

FIGS. 21 and 22 illustrate a still further storage system 440. The storage system 440 includes a vibration generator 442 and a tray/outer packaging 444. The tray/outer packaging 444 may be similar to that illustrated in FIGS. 15 and 16, in that the tray/outer packaging 444 may include a tray having at least one recess 446 in which at least one syringe 448 is disposed and a cover having a filler or deformable member that cooperates with the tray to maintain the syringe 448 in the recess 446. While the tray/outer packaging 444 has a cylindrical shape as illustrated in FIG. 21, this is by way of illustration and not by way of limitation.

As best seen in FIG. 22, the tray 444 may include one or more transducers 450 disposed about the syringe 448. Each transducer 450 may have a spring 452 associated therewith to ensure acoustic coupling with the syringe 448. A controller or drive circuit 454 is coupled to each of the transducers 450, and operates the transducers 450 cause a vibratory motion to be applied to the syringe 448 so as to cause a motion in the product disposed within the syringe 448. Multiple transducers 450 operating at multiple frequencies can be used to set up standing waves to enhance suspension of the cells; the position of the transducers 450 may also be adjusted to set up the standing waves or to physically amplify the signal. Furthermore, frequency sweeps may be used to move the waves so as to cause enhanced suspension and movement. The controller 454 and/or transducers 450 may be coupled to a power supply 456 that may be used to power the controller 454 and/or the transducers 450.

As set forth above, the disclosed device includes the aspects set forth below.

In accordance with one aspect, a storage system for at least one syringe is provided, the syringe including a barrel with first and second barrel ends, a tip disposed at the first barrel end, and a stopper disposed between the first and second barrel ends. The system may include a tray having at least one recess in which the at least one syringe is disposed. The system may also include a tool attached to the stopper through the second barrel end to limit the movement of the stopper toward either one or both of the first and second barrel ends. The tool may have a first end attached to the stopper and a second end attached to or abutting the barrel or a surface of the at least one recess, the first end being selectively adjustable relative to the second end to vary the distance between the first and second ends of the tool.

In accordance with another aspect, the tool may include a shaft having first and second shaft sections, a first end of the first shaft section attached to the stopper, a second end of the first shaft section threadingly engaging a first end of the second shaft section, and a second end of the second shaft section abutting a surface of the at least one recess.

In accordance with another aspect, the syringe may have a rim disposed at the second barrel end, and the tool may include a shaft having a first shaft end attached to the stopper and a second shaft end, and a wheel abutting the rim of the syringe and having a passage through which the shaft is disposed, the passage threadingly engaging the shaft.

In accordance with another aspect, the tool may include a shaft having a first shaft end attached to the stopper and a second shaft end, an inner collar with the shaft disposed within the inner collar and the inner collar having a first inner collar end abutting the second shaft end, and an outer collar with the inner collar disposed within the outer collar and the outer collar having a first outer collar end threadingly engaging a second inner collar end and a second outer collar end attached to the barrel.

In a further aspect, a storage system may include a tray having at least one recess in which at least one syringe is disposed, the syringe including a barrel with first and second barrel ends, and a stopper fixedly disposed between the first and second barrel ends. The system may further include a motion generator attached externally to the at least one syringe, the motion generator being one of at least a vibration generator and a rotating frame.

In accordance with another aspect, the vibration generator may include a plurality of transducers disposed along the barrel between the first and second barrel ends and a controller coupled to the transducers to selectively activate the transducers.

In accordance with another aspect, the rotating frame may include a circular table having first and second opposing faces bounded by a circular rim, and an arm attached at a first end to the first face and at a second end to a pivot, the tray attached to the second face of the circular table.

In accordance with another aspect, the rotating frame may include a shaft disposed within the housing having an outer shaft surface and a drive attached to the shaft, the tray has a cylindrical shape and is disposed between an inner housing surface of a tubular housing and the outer shaft surface with tray abutting the inner housing surface and the outer shaft surface.

Thus, an improved syringe storage tray has been disclosed. The description provided above is intended for illustrative purposes only, and is not intended to limit the scope of the disclosure to any specific embodiment described herein.

The invention claimed is:

1. A storage system comprising:
 a syringe, comprising:
  a barrel with first and second barrel ends, the second barrel end proximate to a dispensing end of the syringe and the first barrel end opposite the second end;
  a plunger tip disposed and movable between the first and second barrel ends; and
  a plunger engaging the plunger tip;
 a tray comprising at least one recess in which the syringe is disposed; and
 a tool comprising:
  a plunger element comprising an inner collar with the plunger disposed within the inner collar and the inner collar having a first inner collar end abutting a second end of the plunger opposite the plunger tip, and engaging the plunger; and
  a wheel engaging the plunger element to at least one of prevent movement of the plunger tip toward either one or both of the first and second barrel ends, and be selectively adjustable relative to the first and second barrel ends to vary the distance between the plunger tip and the first and second barrel ends, comprising an outer collar disposed around the inner collar and the outer collar having a first outer collar end threadingly engaging the inner collar and a second outer collar end attached to the barrel, and
  wherein the wheel is at least one of attached to or abutting the first barrel end and a surface of the at least one recess.

* * * * *